(12) United States Patent
Leak

(10) Patent No.: US 12,150,682 B2
(45) Date of Patent: Nov. 26, 2024

(54) BONE FIXATION SYSTEM WITH FASTENERS AND A REMOVAL TOOL FOR DECOUPLING OF THE FASTENERS

(71) Applicant: Leith Medical, LLC, Austin, TX (US)

(72) Inventor: Timothy Leak, Austin, TX (US)

(73) Assignee: LEITH MEDICAL, LLC, Austin, TX (US)

( * ) Notice: Subject to any disclaimer, the term of this patent is extended or adjusted under 35 U.S.C. 154(b) by 0 days.

(21) Appl. No.: 18/353,945

(22) Filed: Jul. 18, 2023

(65) Prior Publication Data

US 2023/0355288 A1 Nov. 9, 2023

Related U.S. Application Data

(62) Division of application No. 17/068,920, filed on Oct. 13, 2020, now Pat. No. 11,744,626.
(Continued)

(51) Int. Cl.
*A61B 17/80* (2006.01)
*A61B 17/88* (2006.01)
*A61B 17/86* (2006.01)

(52) U.S. Cl.
CPC ...... *A61B 17/8047* (2013.01); *A61B 17/8057* (2013.01); *A61B 17/808* (2013.01);
(Continued)

(58) Field of Classification Search
CPC ............ A61B 17/7059; A61B 17/8033; A61B 17/8042; A61B 17/8047; A61B 17/8052;
(Continued)

(56) References Cited

U.S. PATENT DOCUMENTS 5,370,646 A 12/1994 Reese
5,501,684 A 3/1996 Schlepper
(Continued)

FOREIGN PATENT DOCUMENTS

WO 2007/056516 A2 5/2007
WO 2014/062690 A1 4/2014
(Continued)

OTHER PUBLICATIONS

International Search Report and Written Opinion of International Application No. PCT/US2020/055303, mailing date: Feb. 19, 2021, 21 pages.
(Continued)

*Primary Examiner* — Larry E Waggle, Jr.
(74) *Attorney, Agent, or Firm* — Slayden Grubert Beard PLLC

(57) ABSTRACT

A bone fixation assembly is disclosed. The bone fixation assembly may include a bone fixation plate including a fastener hole and a cavity adjacent to the fastener hole. The bone fixation assembly may also include a clip. The clip may include a body having a partial circular shape, the body positioned at least partially in the cavity. The clip may further include a plurality of tabs extending inward relative to the partial circular shape of the body, each tab having a convex shape extending inward relative to the partial circular shape of the body, wherein the body and the plurality of tabs are positioned below a top surface of the bone fixation plate.

8 Claims, 19 Drawing Sheets

Related U.S. Application Data

(60) Provisional application No. 63/044,179, filed on Jun. 25, 2020, provisional application No. 62/914,749, filed on Oct. 14, 2019.

(52) U.S. Cl.
CPC ............ *A61B 17/809* (2013.01); *A61B 17/88* (2013.01); *A61B 17/888* (2013.01); *A61B 17/8888* (2013.01); *A61B 17/8615* (2013.01)

(58) Field of Classification Search
CPC ..... A61B 17/808; A61B 17/88; A61B 17/888; A61B 17/8888
See application file for complete search history.

(56) References Cited

U.S. PATENT DOCUMENTS

| | | |
|---|---|---|
| 5,520,690 A | 5/1996 | Errico |
| 5,578,034 A | 11/1996 | Estes |
| 5,902,303 A | 5/1999 | Eckhof |
| 5,954,722 A | 9/1999 | Bono |
| 6,235,033 B1 | 5/2001 | Brace |
| 6,241,731 B1 | 6/2001 | Fiz |
| 6,261,291 B1 | 7/2001 | Talaber |
| 6,599,290 B2 * | 7/2003 | Bailey ............... A61B 17/8888 606/256 |
| 6,602,255 B1 | 8/2003 | Campbell |
| 6,884,242 B2 | 4/2005 | LeHuec |
| 7,001,389 B1 | 2/2006 | Navarro |
| D603,510 S | 11/2009 | Kriska |
| 7,766,917 B2 | 8/2010 | Kugler |
| 7,766,947 B2 | 8/2010 | Hawkes |
| 7,963,982 B2 | 6/2011 | Kirschman |
| 7,981,140 B2 | 7/2011 | Burkhart |
| 8,012,174 B2 | 9/2011 | ElAttrache et al. |
| 8,100,955 B2 | 1/2012 | Blain |
| 8,202,296 B2 | 6/2012 | Burkhart |
| 8,202,297 B2 | 6/2012 | Burkhart |
| 8,231,653 B2 | 7/2012 | Dreyfuss |
| 8,348,975 B2 | 1/2013 | Dreyfuss |
| 8,388,665 B2 | 3/2013 | Eberlein |
| 8,465,522 B2 | 6/2013 | Burkhart |
| 8,506,607 B2 | 8/2013 | Eckhof et al. |
| 8,562,656 B2 | 10/2013 | Humphreys |
| 8,591,578 B2 | 11/2013 | Albertorio et al. |
| 8,628,573 B2 | 1/2014 | Roller et al. |
| 8,663,279 B2 | 3/2014 | Burkhart et al. |
| 8,784,459 B2 | 7/2014 | Kaufman et al. |
| 8,858,560 B2 | 10/2014 | Bradley et al. |
| 8,961,569 B2 | 2/2015 | Kaufman et al. |
| 8,986,346 B2 | 3/2015 | Dreyfuss |
| 9,044,273 B2 * | 6/2015 | Richelsoph ........ A61B 17/7074 |
| 9,107,653 B2 | 8/2015 | Sullivan |
| 9,113,859 B2 | 8/2015 | Dooney, Jr. et al. |
| 9,179,950 B2 | 11/2015 | Zajac et al. |
| 9,204,960 B2 | 12/2015 | Albertorio et al. |
| 9,326,844 B2 | 5/2016 | Schmieding et al. |
| 9,332,979 B2 | 5/2016 | Sullivan |
| 9,345,471 B2 | 5/2016 | Sullivan |
| 9,421,086 B2 | 8/2016 | Roller et al. |
| 9,463,011 B2 | 10/2016 | Dreyfuss et al. |
| 9,504,462 B2 | 11/2016 | Dooney, Jr. et al. |
| 9,526,489 B2 | 12/2016 | Burkhart |
| 9,615,821 B2 | 4/2017 | Sullivan |
| 9,642,610 B2 | 5/2017 | Albertorio et al. |
| 9,687,222 B2 | 6/2017 | Dreyfuss et al. |
| 9,693,765 B2 | 7/2017 | Sullivan et al. |
| 9,737,292 B2 | 8/2017 | Sullivan et al. |
| 9,801,621 B2 | 10/2017 | Benavitz |
| 9,855,029 B2 | 1/2018 | Sullivan |
| 9,867,607 B2 | 1/2018 | Sullivan |
| 9,913,672 B2 | 3/2018 | Kaufmann |
| 9,943,341 B2 * | 4/2018 | Carnes ................ A61B 17/808 |
| 10,076,407 B2 | 9/2018 | Albertorio et al. |
| 10,085,739 B2 | 10/2018 | Dooney, Jr. et al. |
| 10,105,169 B2 | 10/2018 | Leak et al. |
| 10,172,606 B2 | 1/2019 | Sullivan et al. |
| 10,172,607 B2 | 1/2019 | Burkhart |
| 10,206,670 B2 | 2/2019 | Thornes |
| 10,245,016 B2 | 4/2019 | Zajac et al. |
| 10,251,686 B2 | 4/2019 | Zajac et al. |
| 10,265,060 B2 | 4/2019 | Dooney, Jr. et al. |
| 10,285,801 B2 | 5/2019 | Roller et al. |
| 10,335,136 B2 | 7/2019 | Dooney, Jr. et al. |
| 10,368,855 B2 | 8/2019 | Burkhart |
| 10,398,426 B2 | 9/2019 | Burkhart et al. |
| 10,441,408 B2 | 10/2019 | Dreyfuss et al. |
| 10,448,943 B2 | 10/2019 | Guerra et al. |
| 10,492,776 B2 | 12/2019 | Dreyfuss et al. |
| RE47,811 E | 1/2020 | Sullivan et al. |
| 10,524,775 B2 | 1/2020 | Benedict et al. |
| 10,568,733 B2 | 2/2020 | Park et al. |
| 10,575,842 B2 | 3/2020 | Lund |
| 10,646,327 B2 | 5/2020 | Lund |
| 10,736,620 B2 | 8/2020 | Dreyfuss et al. |
| 10,736,679 B2 | 8/2020 | Leak et al. |
| 2001/0047172 A1 | 11/2001 | Foley |
| 2002/0019634 A1 | 2/2002 | Bonutti |
| 2002/0188297 A1 | 12/2002 | Dakin |
| 2003/0225409 A1 | 12/2003 | Freid |
| 2004/0019353 A1 | 1/2004 | Freid |
| 2004/0127900 A1 | 7/2004 | Konieczynski |
| 2006/0009770 A1 | 1/2006 | Speirs |
| 2006/0264944 A1 | 11/2006 | Cole |
| 2007/0244489 A1 | 10/2007 | Patel |
| 2008/0147127 A1 | 6/2008 | Tipimeni |
| 2008/0287999 A1 | 11/2008 | Markworth |
| 2011/0034925 A1 | 2/2011 | Tipirneni |
| 2011/0172666 A1 | 7/2011 | Heilman |
| 2013/0123841 A1 | 5/2013 | Lyon |
| 2013/0190825 A1 | 7/2013 | Perrow |
| 2015/0094764 A1 * | 4/2015 | Konieczynski .... A61B 17/8047 606/246 |
| 2015/0245859 A1 * | 9/2015 | McMillen .......... A61B 17/7059 606/289 |
| 2015/0359574 A1 | 12/2015 | Black |
| 2016/0081730 A1 | 3/2016 | Black et al. |
| 2016/0213368 A1 | 7/2016 | Stecco |
| 2016/0220286 A1 | 8/2016 | Garvey et al. |
| 2016/0317203 A1 | 11/2016 | Weiman et al. |
| 2016/0317318 A1 | 11/2016 | Carlson et al. |
| 2017/0209140 A1 | 4/2017 | Thornes |
| 2017/0156767 A1 | 6/2017 | Chaudot et al. |
| 2017/0156771 A1 | 6/2017 | Brinker |
| 2017/0202585 A1 | 7/2017 | Leak et al. |
| 2019/0133655 A1 | 5/2019 | Bonutti |
| 2020/0330140 A1 | 10/2020 | Leak et al. |
| 2021/0106367 A1 | 4/2021 | Leak |
| 2021/0106369 A1 | 4/2021 | Leak |

FOREIGN PATENT DOCUMENTS

| | | |
|---|---|---|
| WO | 2014/089534 | 6/2014 |
| WO | 2016/070191 | 5/2016 |
| WO | 2017/196769 | 11/2017 |

OTHER PUBLICATIONS

International Preliminary Report of International Application No. PCT/US2020/055303, mailing date Apr. 28, 2022, 10 pages.

International Preliminary Report and Written Opinion of International Application No. PCT/US2020/055302, mailing date Apr. 28, 2022, 9 pages.

International Search Report and Written Opinion of International Application No. PCT/US2020/055302, mailing date Feb. 10, 2021, 21 pages.

Japanese Office Action, Application No. 2022522241, 13 pages, May 28, 2024.

* cited by examiner

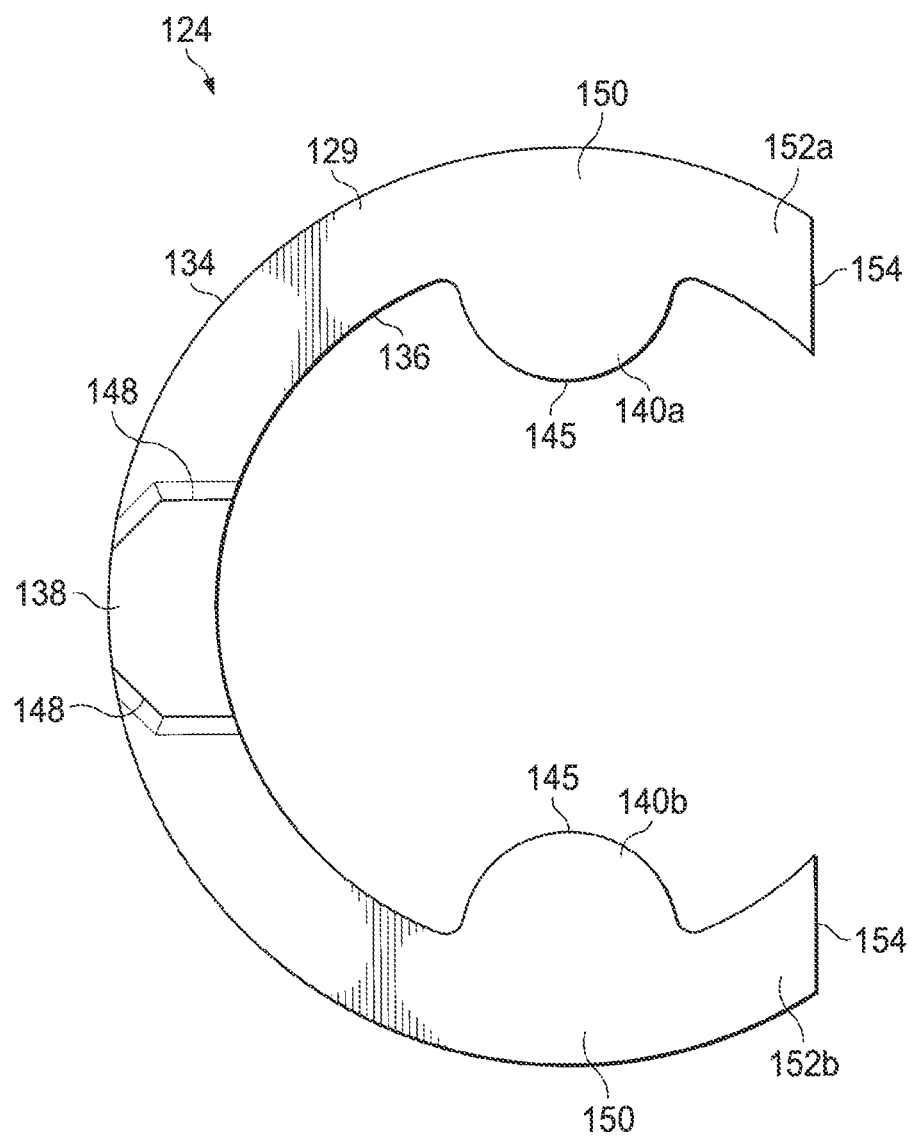
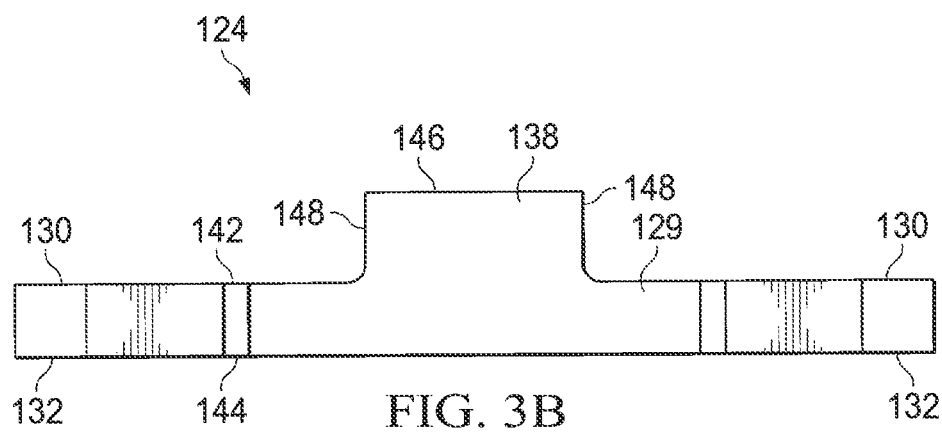
FIG. 3A
FIG. 3B

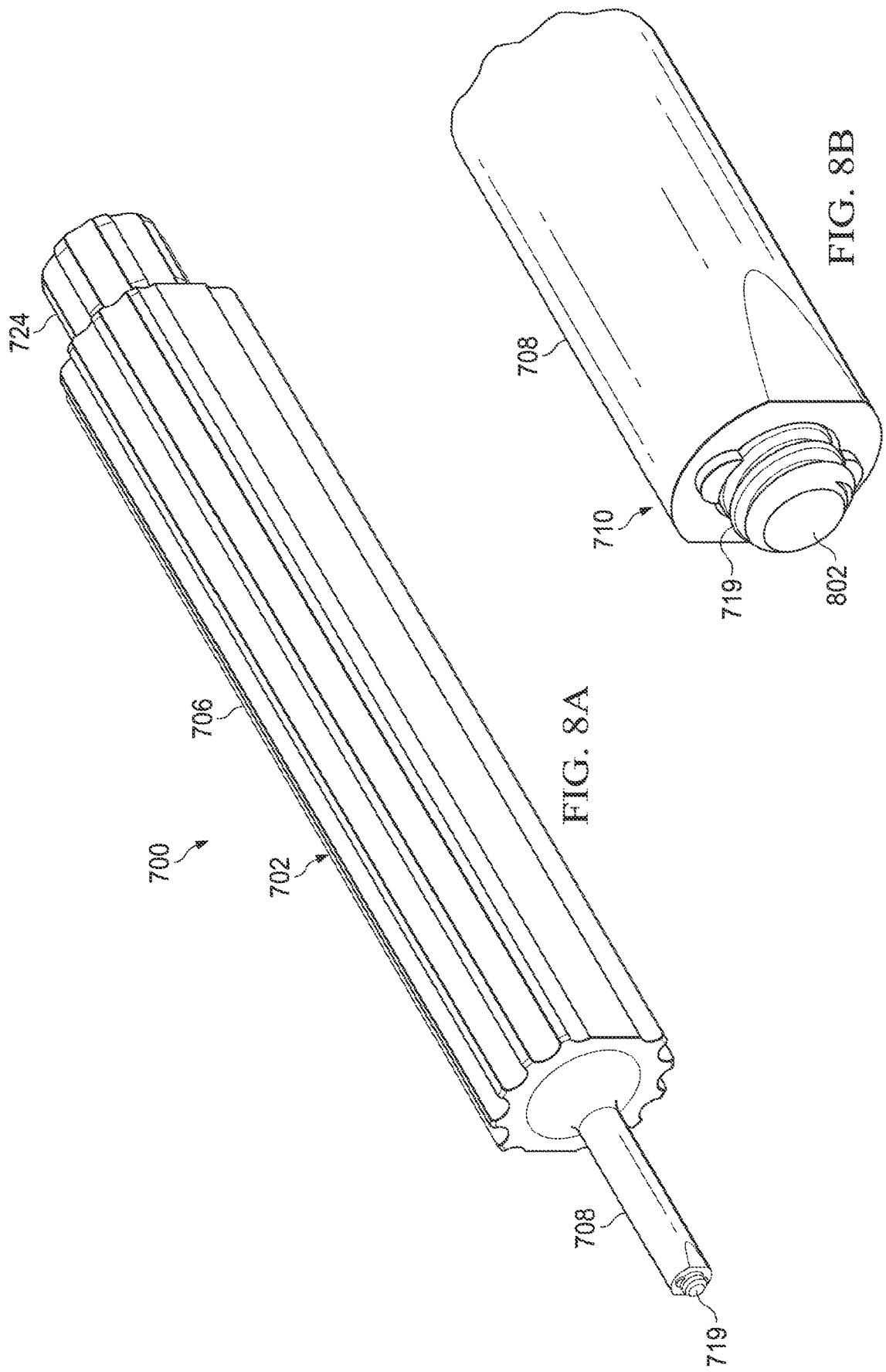

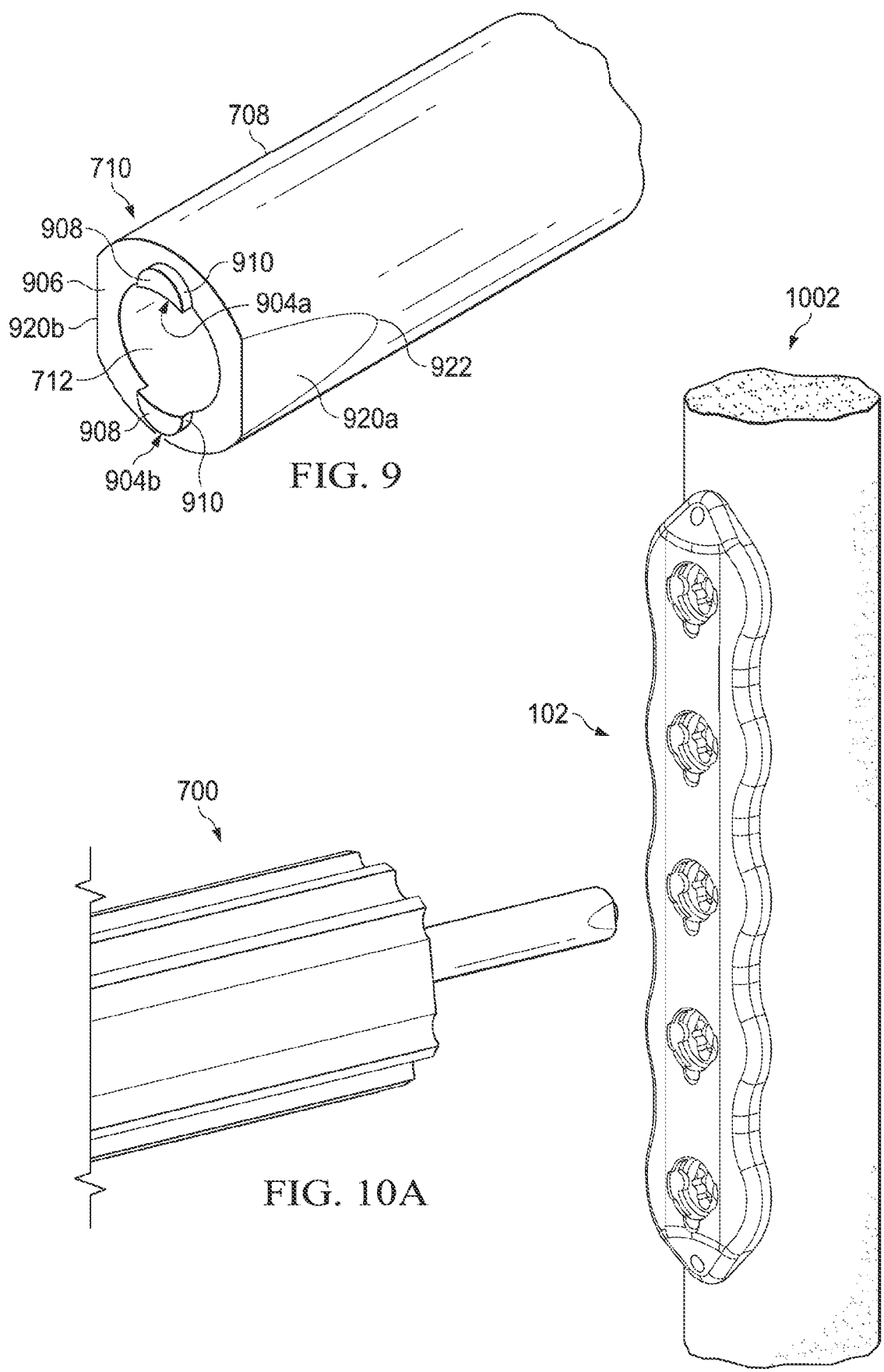

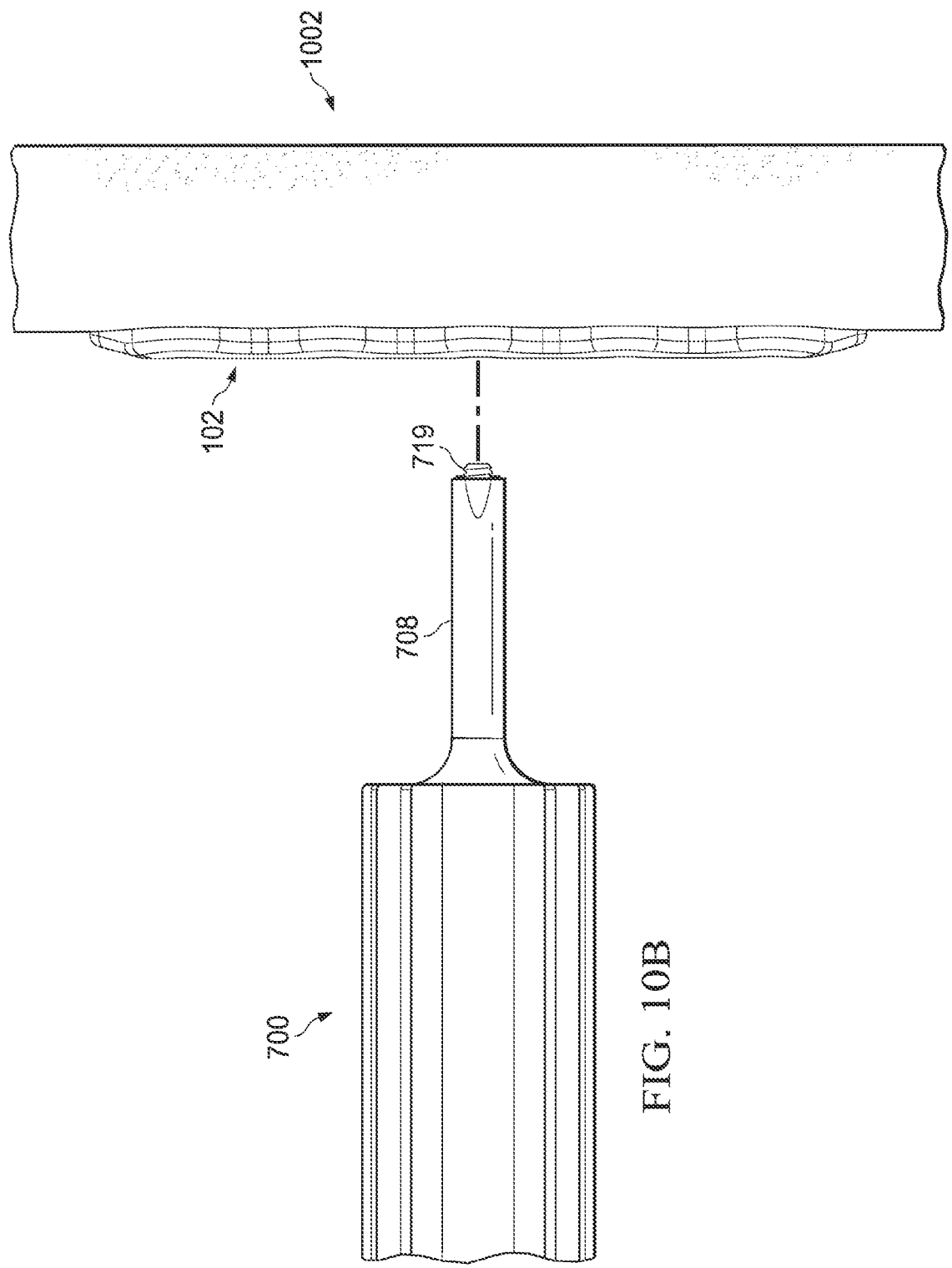

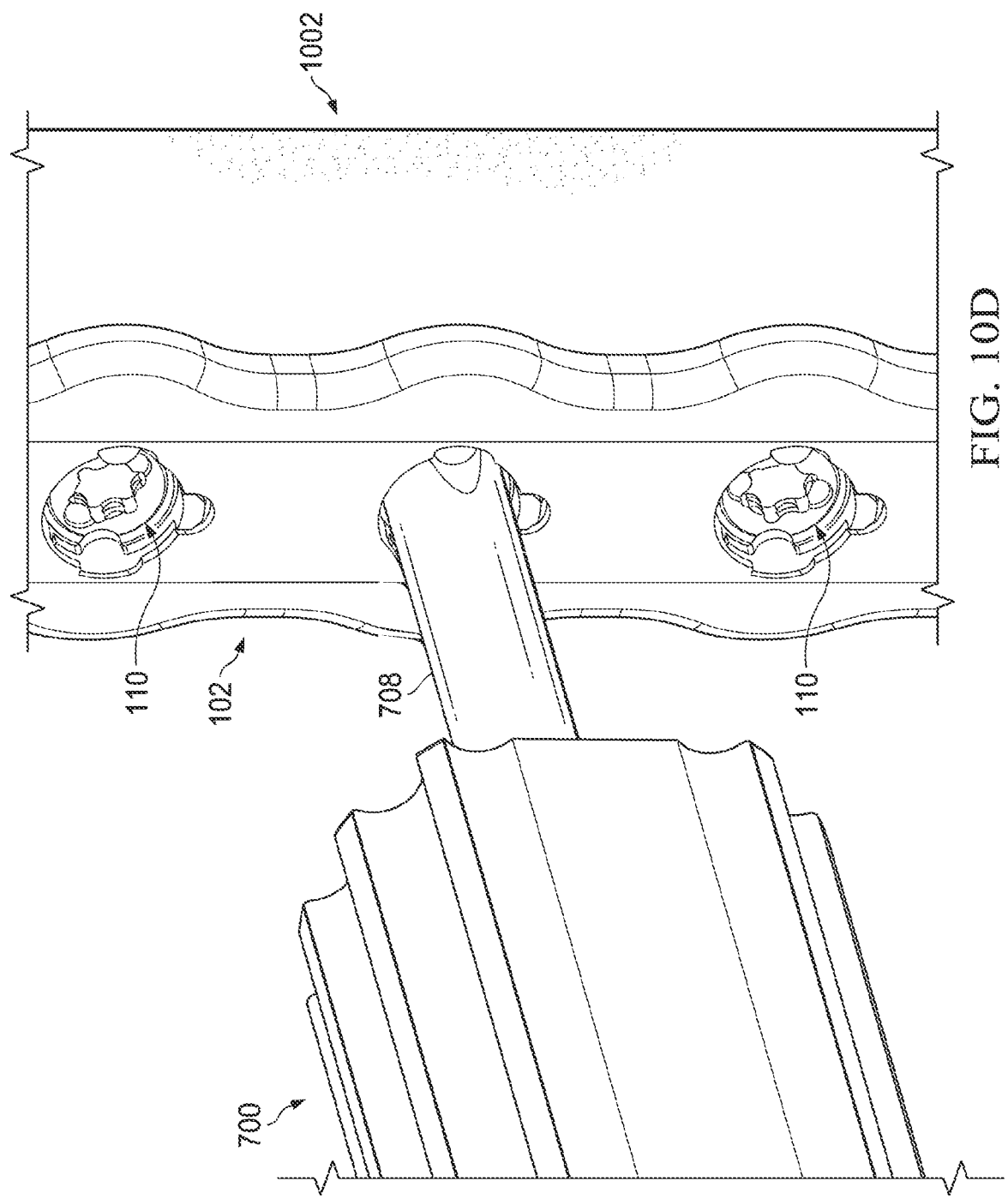

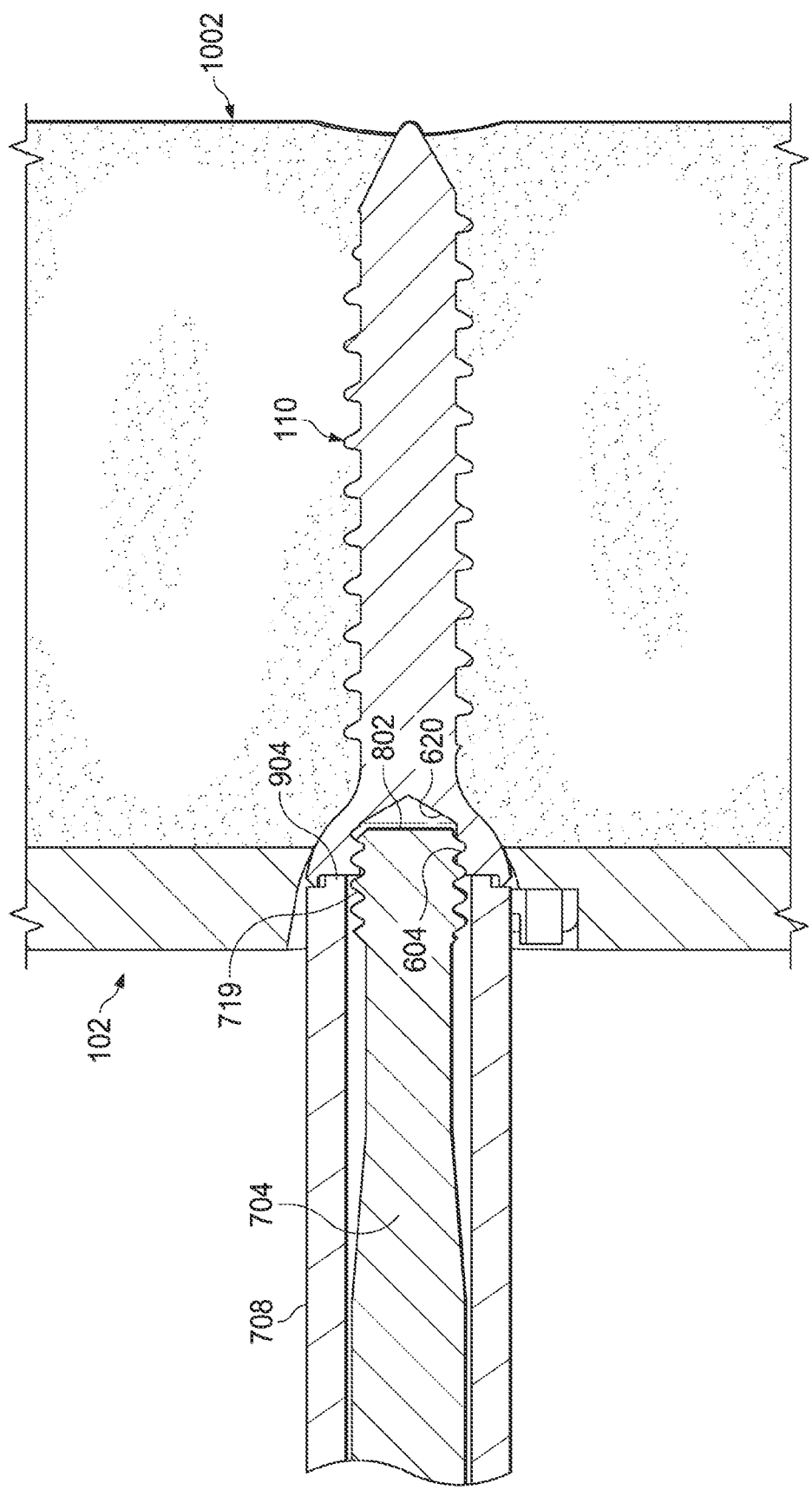

BONE FIXATION SYSTEM WITH FASTENERS AND A REMOVAL TOOL FOR DECOUPLING OF THE FASTENERS

RELATED APPLICATIONS

This application is a Divisional Application of U.S. patent application Ser. No. 17/068,920 filed Oct. 13, 2020, which claims the benefit of U.S. Provisional Application 62/914,749 filed Oct. 14, 2019 and U.S. Provisional Application 63/044,179 filed Jun. 25, 2020, the contents of which are herein incorporated by reference in their entirety.

FIELD OF THE DISCLOSURE

The disclosure relates generally to orthopedic devices, and more specifically, to a bone fixation system with an anti-backout feature and a removal tool.

DESCRIPTION OF THE RELATED ART

For various bone fractures, the use of orthopedic plates is a technique to stabilize the bone as needed for proper healing. Generally, a rigid, often metal plate is placed on the outer surface of the bone across the fracture, and orthopedic screws extend through the plate into the bone on either side of the fracture. The plate offers support and stability to the bone during the healing period.

The term "micromotion" refers to microscopic relative displacements of a loaded intraosseously implanted orthopedic hardware component with respect to the bone surrounding it. Micromotion between the bone and the portion of the orthopedic screws within the bone or vertebrae can cause loosening of one or more orthopedic screws, often called backout. When screw backout occurs, loosening of the entire assembly occurs, thereby diminishing the stability of the set fracture or spinal fusion.

BRIEF DESCRIPTION OF THE DRAWINGS

FIG. 3A is a top down view of an exemplary clip used in a bone fixation plate.

FIG. 3B is a side view of an exemplary clip used in a bone fixation plate.

FIG. 8A is a perspective view of an exemplary removal tool system with an inner portion and an outer portion assembled together.

FIG. 8B illustrates a close up view of a first end of an outer portion of an exemplary removal tool system.

FIG. 9 is a close up view of a shaft of an outer portion of an exemplary removal tool system.

FIG. 10A is a perspective view of an exemplary removal tool system proximate to a bone fixation plate.

FIG. 10B is a side view of an exemplary removal tool system proximate to a bone fixation plate.

FIG. 10D is a close-up view of an exemplary removal tool system engaging with a fastener used with a bone fixation plate.

FIG. 10E is a side cutaway view of an exemplary removal tool system engaging with a fastener used with a bone fixation plate.

DESCRIPTION OF PARTICULAR EMBODIMENT(S)

Figure 1:
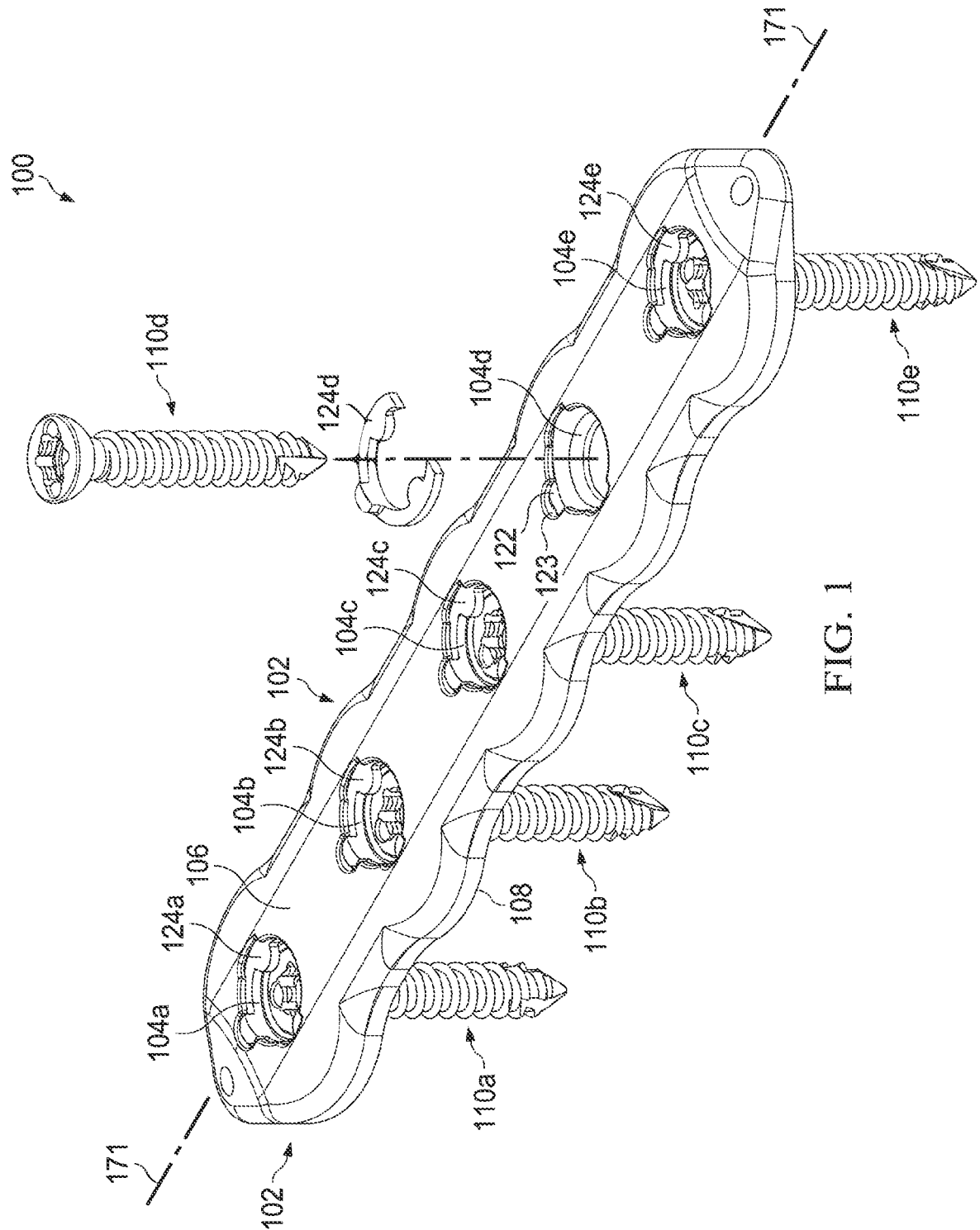
FIG. 1 illustrates a perspective view of an exemplary bone fixation system for stabilization of a bone fracture site, including a bone fixation plate, a fastener, and a clip.

FIG. 1 illustrates a perspective view of an exemplary bone fixation system 100 for stabilization of a bone fracture site. Bone fixation system 100 may include a bone fixation plate 102, fasteners 110a-110e, and clips 124a-124e.

Specifically, the bone fixation plate 102 may include a plurality of fastener holes 104a, 104b, 104c, 104d, 104e (collectively referred to as fastener holes 104). The fastener holes 104 may be positioned through the bone fixation plate 102 from a top surface 106 to a bottom surface 108 of the bone fixation plate 102. As shown in FIG. 1, the bone fixation plate 102 may include five fastener holes 104; however, the bone fixation plate 102 may include any number of fastener holes 104 that is suitable given the length of the bone fixation plate 102. For example, applications that require a shorter bone fixation plate to stabilize a bone may include only two fastener holes 104; and applications that require a longer bone fixation plate to stabilize a bone may include ten or more fastener holes 104. The bone fixation plate 102 may be coupled to a bone (or other body surface such as a tendon, or a ligament) with fasteners 110a, 110b, 110c, 110d, 110e (collectively referred to as fasteners 110). The fasteners 110 may be positioned through respective fastener holes 104. For example, a threaded portion of a fastener 110 may be positioned through a respective fastener hole 104 with a head of fastener 110 ultimately being positioned within the bone fixation plate 102 and underneath a respective clip 124 (for example, from a top down view of the bone fixation system 100) to maintain a desired positioned of the fastener 110, described further herein. As illustrated, the fasteners 110a, 110b, 110c, 110e may be positioned through fastener holes 104a, 104b, 104c, 104e, respectively. However, a subset of the fasteners 110 may be positioned through a subset of the respective fastener holes 104.

As described in further detail below with reference to FIG. 2, the bone fixation plate 102 may include a cavity adjacent to each respective fastener hole to hold a respective clip 124. In some examples, the clips 124 may be inserted into respective cavities adjacent to the respective fastener holes 104 such that a protrusion of the clip 124 is positioned within a notch adjacent to the cavity. The notch may be positioned adjacent to the fastener hole 104 along a midline of the bone fixation plate. The notch may prevent unwanted or undesired rotation of the clip in the cavity. In some examples, the clips 124 may be assembled with bone fixation plate 102 prior to surgery, with the clips 124 in a neutral or unflexed position. During assembly of the clips 124 with bone fixation plate 102, the clips 124 may be flexed inward to facilitate insertion into the fastener holes 104. When tension is released, the clip 124 may transition back to a neutral, unflexed state and be positioned at least in part in the cavity adjacent to the respective fastener hole 104.

During surgery, the fasteners 110 may be inserted downward such that threads of the fasteners 110 engage an underlying body structure. The bone fixation plate 102 may therefore stabilize a fracture in the underlying body structure. As the fastener 110 enters the fastener hole 104, a head of the fastener 110 may apply a wedging force to the respective clip 124. The clip 124 may flex outward in a cavity and toward the sides of the bone fixation plate 102 to allow the head of the fastener 110 to pass through the clip 124 and to be seated into the fastener hole 104. After the head of the fastener 110 passes through the clip 124, the clip 124 may retract and return to its neutral, unflexed shape. For example, as described in further detail below with reference to FIGS. 5A and 5B, tabs of the clip 124 may return to a neutral position over the head of the fastener 110 when the clip 124 returns to its neutral, unflexed shape. Thus, the clip 124 maintains the positioning of the fastener 110 in the body structure and minimizes and/or prevents backout of the fastener 110.

In some examples, the number and/or collective size of openings in the top surface 106 of the bone fixation plate 102 may be minimized in order to optimize the structural strength of the bone fixation plate 102. For example, the fastener holes 104 may be of a minimal size to allow assembly of the clips 124 with bone fixation plate 102 and to allow ingression of the fasteners 110 therethrough. In some embodiments, fastener holes 104 may each include only a single notch 122 interrupting the top surface 106 of the bone fixation plate 102. By minimizing the interruption of the surface area of the top surface 106 of the bone fixation plate 102, a structural strength of the bone fixation plate 102 is increased. And as shown in FIG. 1, the notches 122 for the respective fastener holes 104 may, in some examples, be located along a midline 171 of the bone fixation plate 102 to further optimize the structural strength of the bone fixation plate 102.

Figure 2:
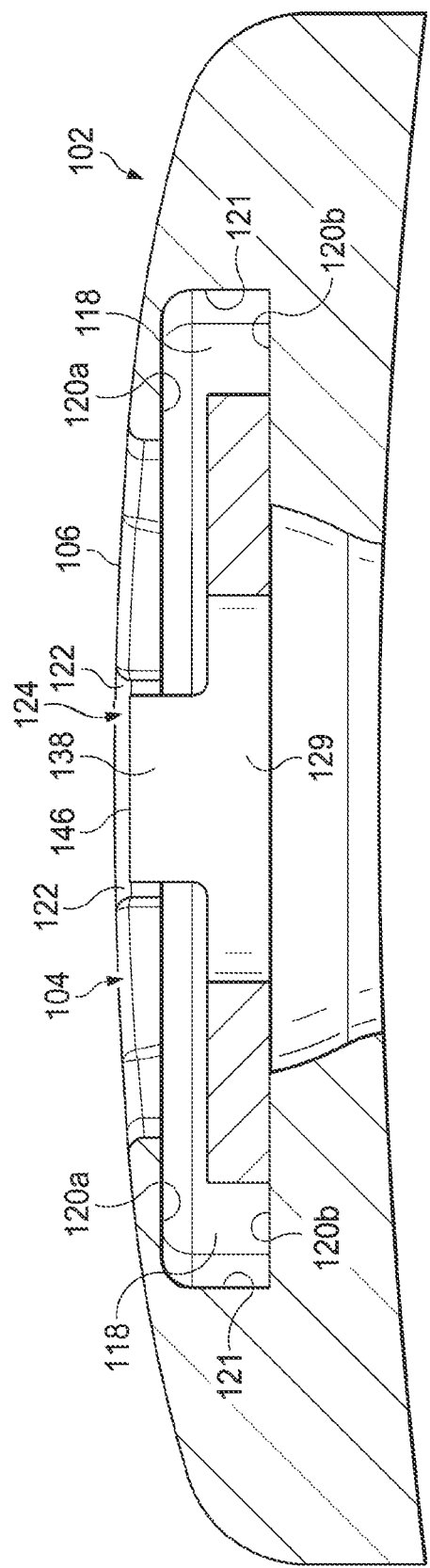
FIG. 2 illustrates a side cutaway view of an exemplary bone fixation system including a bone fixation plate, a fastener, and clip.

FIG. 2 illustrates a side cut away view of an exemplary bone fixation plate 102. Referring to FIGS. 1 and 2, a cavity 118 may be formed along the sidewall of the fastener hole 104. As shown in FIG. 2, the cavity 118 may extend between a first internal surface 120a and a second internal surface 120b (collectively referred to as internal surfaces 120). Further, the cavity 118 may extend between an internal side surface 121 that extends around an internal circumference of the fastener hole 104.

Referring back to FIG. 1, the bone fixation plate 102 may include a notch 122 adjacent to each of the fastener holes 104 (for illustrative clarity purposes, only notch 122 of hole 104d is labelled in FIG. 1). The notch 122 may extend between a top surface of the bone fixation plate 102 and a cavity 118 adjacent to the fastener hole 104. The notch 122 may include a notch surface 123. In some examples, the notch surface 123 may have a semi-circular shape. The notch surface 123 may also be implemented with any shape suitable to engage a protrusion of the clip 124 as described in further detail below. Referring again to the side cutaway view in FIG. 2, the notch 122 may extend between the top surface 106 of the bone fixation plate 102 and the first internal surface 120a of cavity 118.

As shown in FIG. 1, the bone fixation system 100 may include clips 124a, 124b, 124c, 124d, 124e (collectively referred to as clips 124). The clips 124 may be positioned wholly or in part within the cavity 118 for each of the respective fastener holes 104. The cavity 118 may be radially-oriented with respect to the respective fastener hole 104. For example, the cavity 118 adjacent to each respective fastener hole 104 may be circular, or at least, partially circular (for example, semi-circular). The cavities 118 may have a first radius and the clips 124 may have a second radius. The first radius of the cavity 118 may be larger than the second radius of the clip 124. Thus, the clips 124 may be allowed to flex in an outward direction, but within the cavity 118, to allow passage of the head of the fastener while a fastener is either being inserted during surgery or removed during a removal process.

Figure 3C:
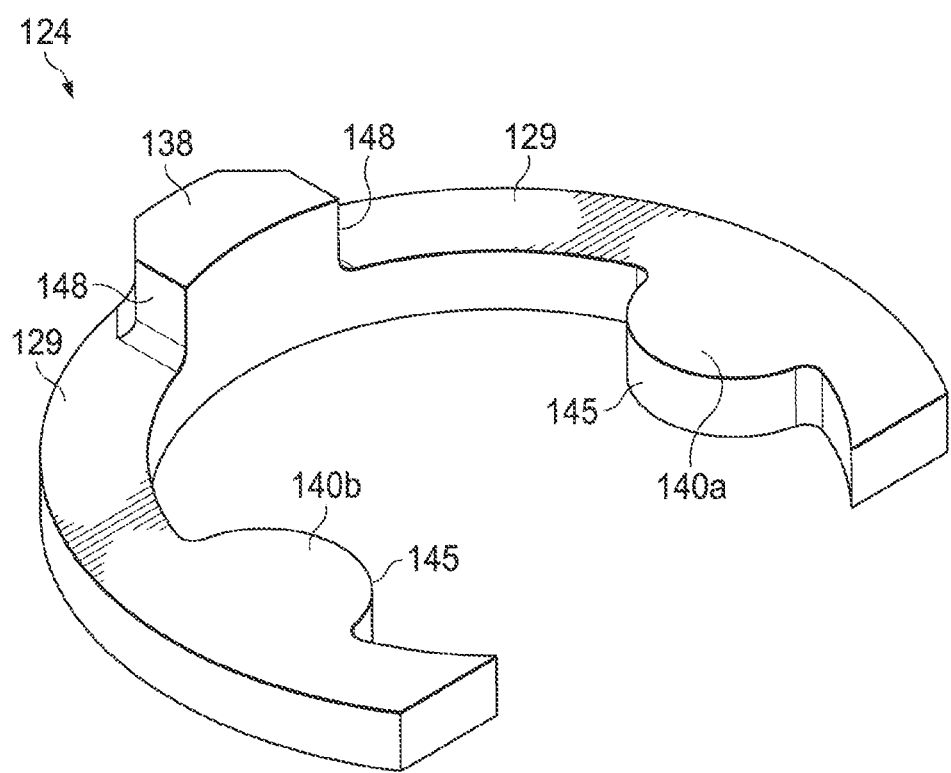
FIG. 3C is a perspective view of an exemplary clip used in a bone fixation plate.

FIG. 3A is a top down view of an exemplary clip 124 that may be used with a bone fixation plate such as the bone fixation plate 102 illustrated in FIG. 1. FIG. 3B is a side view of an exemplary clip 124 that may be used with a bone fixation plate such as the bone fixation plate 102 illustrated in FIG. 1. FIG. 3C is a perspective view of an exemplary clip 124 that may be used with a bone fixation plate such as the bone fixation plate 102 illustrated in FIG. 1. Referring collectively to FIGS. 1, 3A, 3B, and 3C, the clips 124 may include a body 129, a top surface 130, and a bottom surface 132 opposite to the top surface 130. Further, the clips 124 may include an exterior surface 134 and an interior surface 136. Also, each clip 124 may include a protrusion 138 and tabs 140a, 140b (collectively referred to as tabs 140). The protrusion 138 and the tabs 140 may extend from the body 129. In some examples, the clips 124 include two tabs as shown in FIGS. 3A and 3C. Depending on the application desired, the clips 124 may also have any number of tabs suitable to engage with the fastener 110.

The tabs 140 may extend inward from the interior surface 136, and extend between the top surface 130 and the bottom surface 132 of the clip 124. A top surface 142 of the tabs 140 may be substantially co-planar with the top surface 130; and a bottom surface 144 of the tabs 140 may be substantially co-planar with the bottom surface 132. That is, in some examples, a thickness of the body 129 may be substantially the same as the thickness of the tabs 140. In such examples, the different portions of the clip 124, excluding the protrusion 138, may have a uniform thickness.

In some examples, one or both of the top surface 130 and bottom surface 132 of the body 129 may extend beyond the respective top surface 142 and the bottom surface 144 of the tabs 140 such that the thickness of the body 129 is greater than a thickness of the tabs 140. In other examples, one or both of the top surface 142 and the bottom surface 144 of the tabs 140 may be extend beyond the respective top surface 130 and bottom surface of the body 129 such that the thickness of the body 129 may be less than a thickness of the tabs.

In some examples, a height of the tabs 140 defined between top surface 142 and the bottom surface 144 of the tabs 140 is configured to fit within a height of the cavities 118 of the fastener holes 104 defined between the internal surfaces 120 of the cavities 118.

Referring back to FIGS. 1 and 2, the clips 124 may maintain a position of the fasteners 110 after the fasteners 110 are coupled through the bone fixation plate 102 and within an adjacent body surface (for example, a bone). In some examples, prior to the fasteners 110 entering the fastener holes 104, the clips 124 may be in a neutral or unflexed position in the respective cavities 118. For example, the body of a clip 124 may be positioned at least in part in a cavity 118 with the tabs of the clip protruding inward into the fastener hole 104.

Referring to FIG. 1, as a fastener 110 enters a fastener hole 104, a tapered surface on the head of fastener 110 may contact the tabs of clip 124. The head of the fastener 110 may thus exert a wedging force on the tabs of the clip 124. The wedging force may flex the clip 124 outward and further into the cavity 118 adjacent to the fastener hole 104. In other words, as the fastener 110 translates through the fastener hole 104 (for example, as the fastener 110 is "screwed into" the adjacent body surface), a head of the fastener 110 forces the clip 124 to flex (from previously being unflexed) to allow passage of the head of the fastener 110.

As the fastener 110 continues the translation through the fastener hole 104, the fastener 110 may come to a seated position in the bone fixation plate 102. Once the head of the fastener 110 is past the tabs 140 of the clip 124, the clip 124 may return to its neutral or unflexed state. As such, a head of the fastener 110, may be positioned underneath the clip 124, and specifically, underneath the tabs 140 of the clip 124. More specifically, the head of the fastener 110 may be positioned between the clip 124 and the bottom surface 108 of the bone fixation plate 102 such that the clip 124 maintains the position of the fastener 110 (for example, maintains the coupling of the fastener 110 and the body surface). In this state, the tabs 140 of the clip 124 may maintain the seated positioning of the fastener 110 and minimize and/or prevent backout of the fastener 110 from the bone fixation plate 102 and the underlying body structure. In other words, the clip 124, and in particular the tabs 140 of the clip 124, may maintain the head of the fastener 110 between the clips 124 and the bottom surface 108 of the bone fixation plate 102. The clip 124 may thus prevent the fastener 110 from egressing back out through the fastener hole 104 away from the bone fixation plate 102. For example, the clip 124 may prevent unwanted backout of the fastener 110 due to micromotion.

As shown in FIGS. 3A and 3C, an outer surface 145 of the tabs 140 may have a convex shape extending inward relative to the partial circular shape of the body 129 of the clip 124. In some embodiments, the tabs 140 may extend inward in a circular (for example, a semi-circle) shape. The tabs 140 of the clip 124 may also be formed with other shapes suitable to maintain a position of the fastener 110 after the fastener 110 has been inserted through the bone fixation plate 102. For example, the tabs 140 of the clip 124 may include a triangular, square, or rectangular shape that maintains the position of the fastener 110 after the fastener 110 has been inserted through the bone fixation plate 102. In some embodiments, for example where the tabs 140 have a triangular, square, or rectangular shape, the tabs 140 may include rounded-off corners. The circular shape, or rounded-off corners of other example shapes, may help the tab 140 maintain consistent contact with a top surface of the head of the fastener 110 when the fastener 110 has been inserted through the bone fixation plate, for example, at an angle as described below with reference to FIGS. 5A and 5B.

In some examples, the clip 124 may minimize and/or prevent any loosening or backout of the fasteners 110 (for example, as a result of micromotion). Specifically, after appropriately positioning the fastener 110 through the fastener hole 104 and the adjacent body surface, the clip 124 may reduce unwanted rotation of the fastener 110. The clip 124 may thus minimize and/or prevent the fastener 110 from egressing back out through the fastener hole 104 away from the bone fixation plate 102. In other words, the clip 124 may prevent unwanted backout of the fastener 110 due to micromotion.

In some embodiments, the clip 124 may be formed with a metal or a metal alloy having superelastic properties. In other words, the clip 124 may be formed with a resiliently flexible material that may flex under force but then return to its unflexed state when the force is removed. For example, the clip 124 may be formed with a nickel-titanium alloy referred to as nitinol. In other examples, the clip 124 may be formed from titanium, stainless steel, or medical grade plastic. In some examples, the body 129 of the clip 124 may have a thickness defined between the top surface 130 and the bottom surface 132. The thickness of the body 129 of the clip 124 may allow for sufficient flexing of the clip 124 from the neutral or unflexed state to the flexed state. Further, the thickness of the body 129 and the tabs 140 of the clip 124 may also allow for sufficient strength of the clip 124 to minimize and/or prevent anti-backout of the fastener 110 when the fastener 110 is coupled to the bone fixation plate 102. In some examples, the thickness of the body 129 of the clip 124 may be between 0.010 inches to 0.040 inches. In some examples, the thickness of the body 129 of the clip may be between 0.015 inches and 0.025 inches.

Referring back to FIGS. 1 and 2, a diameter of the cavity 118 may accommodate the clip 124 when the clip 124 is in either of a flexed or an unflexed state. As mentioned previously, the diameter of the clip 124 is increased when the fastener 110 engages with the clip 124 when entering the fastener hole 104. The diameter of the cavity 118 between the internal side surface 121 may accommodate such increase in the diameter of the clip 124 when the fastener 110 passes through the clip 124.

As shown in FIGS. 2, 3A, 3B, and 3C, a protrusion 138 may extend from the body 129 of the clip 124. And referring back to FIG. 1, the bone fixation plate 102 may include a notch 122 adjacent to the fastener hole 104. The notch 122 of the bone fixation plate 102 may be shaped to correspond to the shape of the protrusion 138 of clip 124. In some examples, the protrusion 138 of the clip 124 may engage with the notch 122 of the bone fixation plate 102 to minimize and/or prevent rotation of the clip 124 in the cavity 118 when the clip 124 is positioned in the cavity 118 of the fastener hole 104. In some examples, the notch 122 may be positioned adjacent to the fastener hole 104 along a midline of the bone fixation plate 102.

As shown in FIGS. 2, 3A, 3B, and 3C, the protrusion 138 may include a protrusion side surface 148 extending between the top surface 130 of the body 129 and the top surface 146 of the protrusion 138. When the clip 124 is positioned in the cavity 118 of the fastener hole 104 of the bone fixation plate 102, the protrusion 138 may be positioned within the notch 122 of the fastener hole 104. In some examples, the side surface 148 of the protrusion 138 may be in contact with the notch surface 123 when the clip 124 is positioned in the cavity 118 of the bone fixation plate 102. In some examples, the protrusion 138 may minimize and/or prevent rotation of the clip 124 in the cavity 118 of the fastener hole 104. For example, the protrusion 138 may minimize and/or prevent rotational movement of the clip 124 with respect to the bone fixation plate 102 by contact between the protrusion side surface 148 of the protrusion 138 and the notch surface 123 of the notch 122.

The shape of the side surface 148 of the protrusion 138 may correspond to, or may have the same or similar shape as, the shape of the notch surface 123 of the notch 122. For example, as shown in FIG. 3A, the protrusion side surface 148 may include one or more angles to approximate a curve shape. And referring back to FIG. 1, the approximated curvature may correspond to the curvature of the notch surface 123 within the notch 122 of the fastener hole 104. Although the protrusion 138 is shown in FIG. 3A as having an angled curve shape, the protrusion 138 of the clip 124 and/or the corresponding notch 122 of the bone fixation plate 102 may have any shape suitable for minimizing and/or preventing rotation of the clip 124 when the clip 124 is inserted in the cavity 118 of the bone fixation plate 102. In addition, although the clip 124 is illustrated in FIGS. 3A, 3B, and 3C as including a single protrusion 138, the clip 124 may include any number of protrusions suitable to correspond to one or more of the notches 122 adjacent to a fastener hole 104 to minimize and/or prevent rotation of the clip 124 in the cavity 118.

As shown in FIGS. 3B and 3C, the protrusion top surface 146 may be flat. A height of the protrusion 138 may be defined between the protrusion top surface 146 and the top surface 130 of the body 129 of the clip 124. The height of the protrusion 138 may be configured such that the protrusion top surface 146 is even with or below the top surface 106 of the bone fixation plate 102, as shown in FIG. 2. Thus, after the fastener 110 has been inserted into the fastener hole 104 and through the clip 124, all portions of the fastener 110 and the clip 124 may be contained underneath the top surface 106 of the bone fixation plate 102 (as viewed from a top-down view of the bone fixation plate 102). Thus, trauma to the surrounding tissue may be minimized due to a reduction in post-surgery interference involving the bone fixation plate.

Referring to FIG. 3A, the body 129 of the clip 124 may include a first portion 150 and second portions 152a, 152b (collectively referred to as second portions 152). The second portions 152 of the body 129 may include an extension from the first portion 150 of the body 129 to an end surface 154. With the first portion 150 and the second portions 152, the body 129 of the clip 124 may encompass more than 180 degrees but less than 360 degrees of a circular shape. With a gap between the respective end surfaces 154 of the second portions 152a and 152b (that is, the body encompassing less than 360 degrees of a circular shape), the body 129 of the clip 124 may flex inward or outward. For example, the body 129 of the clip 124 may be resiliently flexible to flex inward or outward. Moreover, in example embodiments where the second portions 152 of the body 129 extend the body 129 substantially more than 180 degrees (for example, 190 degrees or more) around a circular shape, the second portions 152 may improve a stability of the clip 124 in a cavity 118 of the bone fixation plate 102. For example, the extension of the circular shape of the body 129 by the second portions 152 may minimize and/or prevent teetering of the clip 124 inside the cavity 118 of the bone fixation plate 102 when upward and/or downward forces are applied to the tabs 140. In addition, the additional surface area of the clip 124 provided by the second portion 152 may provide additional contact points with the first internal surface 120a of the cavity 118 when the fastener 110 has been inserted through the fastener hole 104, thus providing additional support and strength for the clip 124 to prevent post-surgery backout of a fastener 110 inserted through the bone fixation plate 102. In some examples, the second portions 152a and 152b may each be of substantially the same length between the tabs 140 and the end surface 154. In some examples, the different second portions 152a and 152b may be of differing lengths extending from the first portion. In some examples, the second portions 152 may be co-planar with the first portion 150 of the body 129. In some examples, a thickness of the second portions 152 defined between the top surface 130 and the bottom surface 132 may be substantially the same as a thickness of the first portion 150 defined between the top surface 130 and the bottom surface 132. In some examples, the thickness of the second portions 152 may differ from the thickness of the first portion 150. In some examples, the thickness of each of the second portions 152a and 152b may differ from each other.

Figure 4:
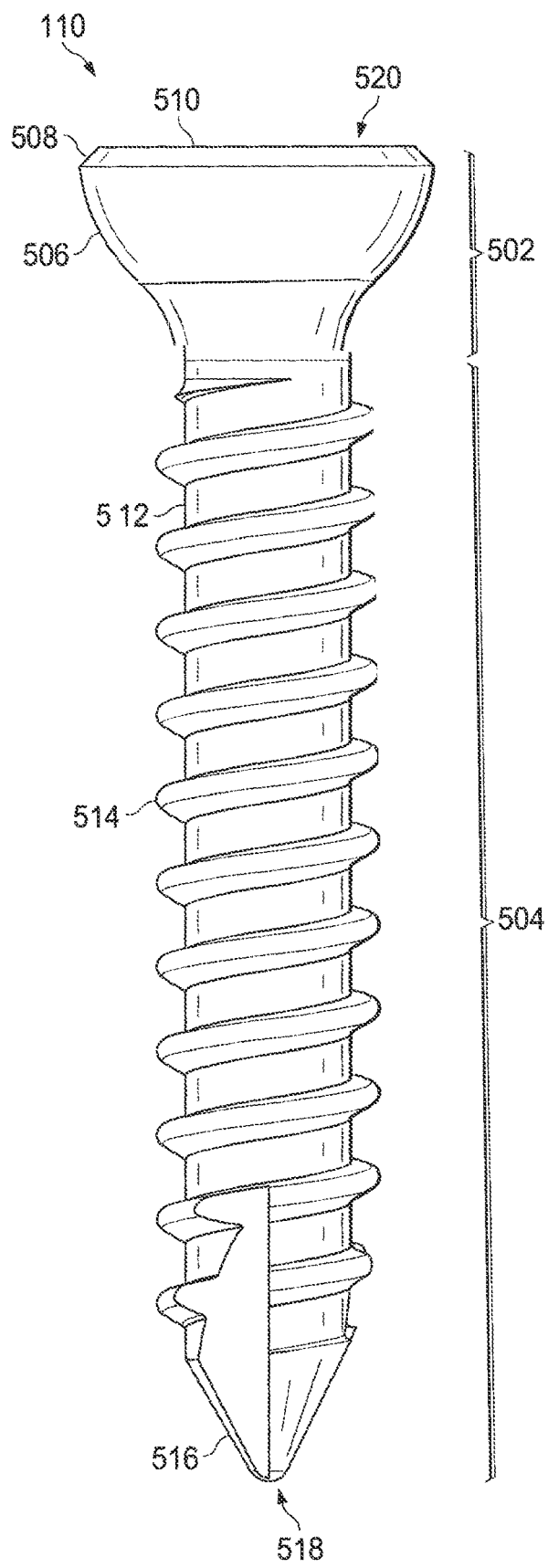
FIG. 4 is a side view of an exemplary fastener used with a bone fixation plate.

FIG. 4 is a side view of an exemplary fastener 110 to be used with the bone fixation plate 102. The fastener 110 may include a head 502 and a body 504. The body 504 may be coupled directly to the head 502. The body 504 may also be coupled to the head 502 indirectly via an intermediate portion (not illustrated in FIG. 4).

The head 502 may be positioned at a first end 520 of the fastener 110. The head 502 may include a spherical tapered portion 506 and a chamfer portion 508. The chamfer portion 508 may have a first diameter at a first surface 510 of the head 502, and a second diameter at an interface between the chamfer portion 508 and the spherical tapered portion 506. The first diameter may be less than the second diameter. In some embodiments, the head 502 may also include an intermediate head portion (not illustrated in FIG. 4) between the chamfer portion 508 and the spherical tapered portion 506. The intermediate head portion may have a cylindrical shape extending the interface between the chamfer portion 508 and the spherical tapered portion 506, and may share the second diameter described directly above.

The body 504 of the fastener 110 may include a shaft 512. The shaft 512 may include screw threads 514. The screw threads 514 may engage with a body surface such as a bone, tendon, or ligament. The body 504 may further include a tip 516. The tip 516 may be conical and positioned at a second end 518 of the fastener 110 opposite to the first end 520 of the fastener 110.

The example embodiment of the fastener 110 in FIG. 4 is illustrated as a fully threaded cancellous screw. In other embodiments, the fastener 110 may be implemented as other types of screws, for example, a partially threaded cancellous screw, a fully threaded cortical screw, a partially threaded cortical screw, a cancellous and cortical screw, and others. For example, fastener 110 may be implemented with threads over substantially the entire length of their shafts, or alternatively with threads over a portion of the length of their shafts, with at least another portion of the length of their shafts unthreaded. In some examples, fastener 110 may be implemented as a cancellous and cortical screw with threads of one type along a distal portion of its shaft and threads of another type along a proximal portion of its shaft. The distal portion may be immediately adjacent to the proximal portion, or the distal portion and the proximal portion may be separated from each other, for example, by an unthreaded portion.

Figure 5A:
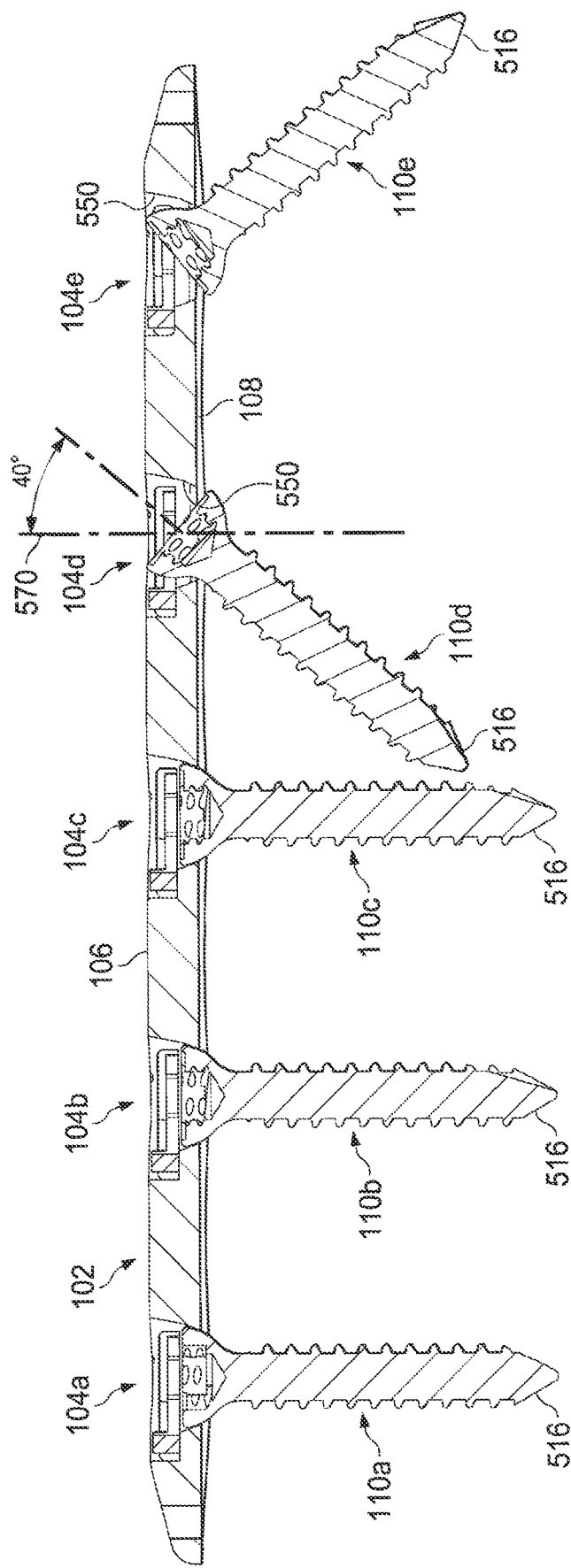
FIG. 5A is a side cut-away view of an exemplary bone fixation system including fasteners having angulation with respect to a bone fixation plate.
Figure 5B:
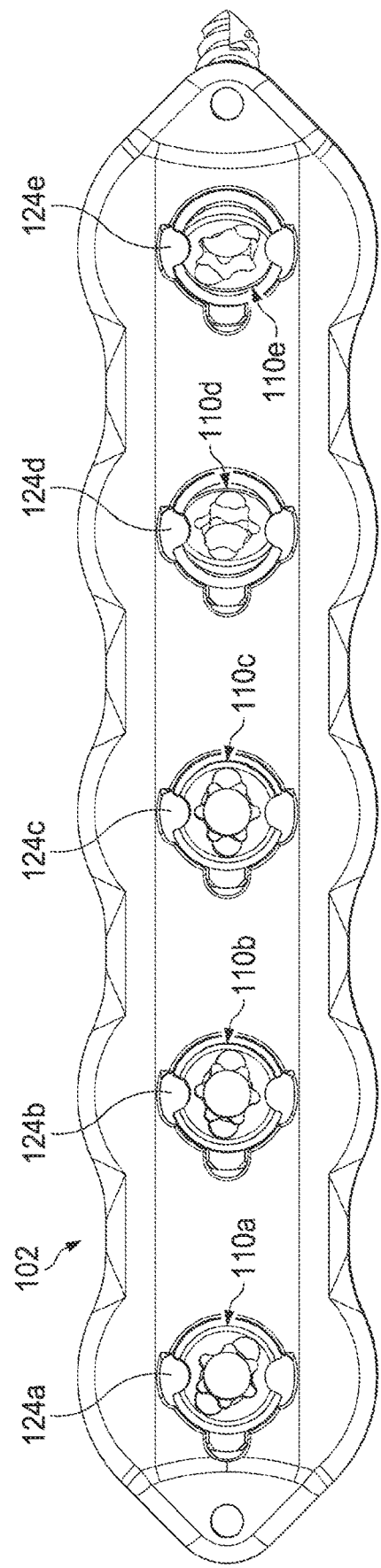
FIG. 5B is a top down view of an exemplary bone fixation system including fasteners having angulation with respect to a bone fixation plate.

FIG. 5A is a side cut-away view of the exemplary fasteners 110 coupled with the bone fixation plate 102. FIG. 5B is a top down view of the exemplary fasteners 110 coupled within the bone fixation plate 102. In the illustrated example, the fasteners 110 are shown positioned through respective fastener holes 104. The clips 124 may maintain the positioning of the fasteners 110 with respect to the bone fixation plate 102 and/or a body surface coupled to the bone fixation plate 102. The clips 124 minimize and/or prevent any loosening or backout of the fasteners 110 that may occur through micromotion.

As the fastener 110 is translated through the fastener hole 104, the head 502 of the fastener 110 may exert a wedging force on the tabs 140 of the clip 124 (shown in FIGS. 3A-C) to flex the clip 124 and thus move the tabs 140 outward and into the cavity 118 (shown in FIG. 2). Specifically, the head 502 of the fastener 110 may exert the wedging force on the tabs 140 of the clip 124 to flex the clip 124 from a neutral, unflexed position to a flexed position such that the diameter of the clips 124 is increased. The body 129 of the clips 124 may be resiliently flexible such that the clips 124 can change states from the neutral or unflexed position to the flexed position. As this diameter of the clips 124 is increased, the tabs 140 of the clips 124 move outward and into the cavity 118 to allow passage of the head 502 of the fastener 110.

The fastener 110 may then come to a final positioning state with respect to the bone fixation plate 102 and the underlying body structure. As such, the head 502 of the fastener 110, as shown in FIG. 4, may be seated in the bone fixation plate 102 underneath the clip 124 and specifically, underneath the tabs 140 of the clip 124. The head of the fastener 110 may be positioned between the clip 124 and the bottom surface 108 of the bone fixation plate 102 such that the clip 124 maintains the position of the respective fastener 110 (for example, maintains the coupling of the fastener 110 and the body surface). Once the head of the fastener 110 is inserted past the tabs 140 of the clip 124, the clip 124 may return to its neutral, unflexed state. The body 129 of the clips 124 may have a spring tension to facilitate the clip 124 retracting back to its neutral, unflexed state after the head of the fastener 110 has passed the clip. After returning the neutral, unflexed state, the tabs 140 of the clip 124 may maintain the seated position of the fastener 110 in the bone fixation plate 102 and may thus minimize and/or prevent backout of the fastener 110 from the bone fixation plate 102 and the underlying body structure. For example, the tabs 140 of the clip 124 may maintain the head 502 of the fastener 110 between the clips 124 and the bottom surface 108 of the bone fixation plate 102. The clip 124 may reduce unwanted rotation of the fastener 110 (for example, backout rotation). The clip 124 may thus prevent the fastener 110 from egressing back out through the fastener hole 104 away from the bone fixation plate 102. For example, the clip 124 may prevent unwanted backout of the fastener 110 due to micromotion.

In some examples, fasteners 110 may be translated through the fastener hole 104 in a direction substantially perpendicular with the bone fixation plate 102, as shown by fasteners 110a, 110b, 110c. The fastener 110 may also be translated through the fastener hole 104 at an angle with respect to the bone fixation plate 102, as shown by fasteners 110d, 110e.

Vertical axis 570 is illustrated in FIG. 5A as extending through fastener hole 104d and substantially perpendicular to the top surface of the bone fixation plate 102 at the location of the respective fastener hole 104d. The sidewall 550 of the fastener hole 104 may be configured with a rounded tapered shape. The sidewall 550 may thus correspond to a spherical tapered portion 506 of the fastener 110 (shown in FIG. 4) to allow the insertion of a fastener 110 either straight down or at an angle. Each of the respective fasteners 110 may have an angulation between 0 and 45 degrees relative to their respective vertical axes. For example, as shown in FIG. 5A, fastener 110d may be inserted at an angle of 40 degrees relative to vertical axis 570. In some embodiments, the taper of sidewall 550 may be symmetric around the vertical axis of the fastener hole 104. The fasteners 110 may thus be inserted at an angle in any direction around the vertical axis 570.

In some applications, a subset of the fasteners 110 may be angled relative to a vertical axis of their respective fastener hole 104. In some applications, each of the fasteners 110 may be angled relative to the vertical axis of their respective fastener hole 104. In some applications, different fasteners 110 may have differing angulation directions and differing angulation degrees with respect to the vertical axis of each respective fastener hole 104.

In some examples, the angulation direction and the angulation degree of a fastener 110 relative to the vertical axis of the respective fastener hole 104 may be determined based on the underlying body structure that the fastener 110 couples to the bone fixation plate 102. For example, the angulation direction and the angulation degree of the fastener 110 relative to the vertical axis of the respective fastener hole 104 may be determined before or during surgery based on the location and/or density of bone matter to which the bone fixation plate 102 is being coupled.

As shown in FIG. 5B, the clips 124 maintain contact with a top surface of their respective fasteners 110 regardless of whether the respective fasteners 110 have been inserted straight down (for example, fasteners 110a, 110b, and 110c) or at an angle (for example, fasteners 110d and 110e). In this state, the tabs of the clip may maintain the final positioning of the fastener 110 and may minimize and/or prevent backout of the fastener, as described in detail above. For fasteners 110 inserted at an angle (for example, fasteners 110d and 110e), a portion of the top surface of the head of the fastener 110 may be rotated and thus project up through an interior of the clip. But, features of the bone fixation plate 102 and fasteners 110 may provide headroom such that the entire top surface of the head of the fastener 110 may still be encompassed below the top surface 106 of the bone fixation plate 102 when the fastener 110 is inserted at a large angle (for example 40 degrees or more).

For example, as shown in FIG. 5A, the fastener holes 104 and their respective sidewalls 550 may be shaped and sized such that a portion of the head of fastener 110 may extend below the bottom surface 108 of the bone fixation plate 102 when the fastener 110 is inserted at large angle (for example, 40 degrees or more) relative to the vertical axis of the fastener hole 104. This may provide additional headroom for the entirety of the head of fastener 110 to fit below the top surface 106 of the bone fixation plate even when fasteners 110 are inserted at large angles. Accordingly, the respective heads of fasteners 110 may be prevented from projecting out from the top surface 106 of bone fixation plate 102 regardless of the angle at which the respective fasteners 110 are inserted. Thus, post-surgery interference involving the bone fixation assembly with surrounding tissue may be minimized regardless of the angle at which the respective fasteners 110 are inserted.

Referring back to FIG. 3C, the tabs 140 of the clip 124 may be rounded. And referring back to FIG. 4, the head of the fastener 110 may include a chamfer portion 508. The rounded shape of the tab 140 and/or the chamfer portion 508 of the head of the fastener 110 may strengthen the contact point of the tab 140 and the fastener 110 when the fastener 110 is inserted at an angle as shown in FIGS. 5A and 5B. For example, the rounded shape of the tab 140 may prevent the tab 140 from contacting the head of the fastener at a point on the tab 140 that is at or near the tip of an acute angle. Likewise, the chamfer portion 508 of the fastener 110 may prevent the fastener 110 from contacting the tab 140 at a point on the head of the fastener 110 that is at or near the tip of an acute angle.

Furthermore, when the fastener 110 is inserted into a fastener hole 104 at an angle, the spherical tapered portion 506 of the fastener 110 may contact sidewalls 550 of the fastener hole 104 at multiple locations of the sidewalls 550. By providing multiple points of contact between the spherical tapered portion 506 of the fastener 110 and the sidewalls 550 of the fastener hole 104, a stability of the fastener 110 with respect to the bone fixation plate 102 is improved. For example, the seating of the fastener 110 within the fastener hole 104 may be improved when there are multiple points of contact between the spherical tapered portion 506 of the fastener 110 and the sidewalls of the fastener hole 104. In some examples, the spherical tapered portion 506 of the fastener 110 allows more than 180 degrees of contact about the head 502 of the fastener 110 with the sidewalls 550.

Figure 6A:
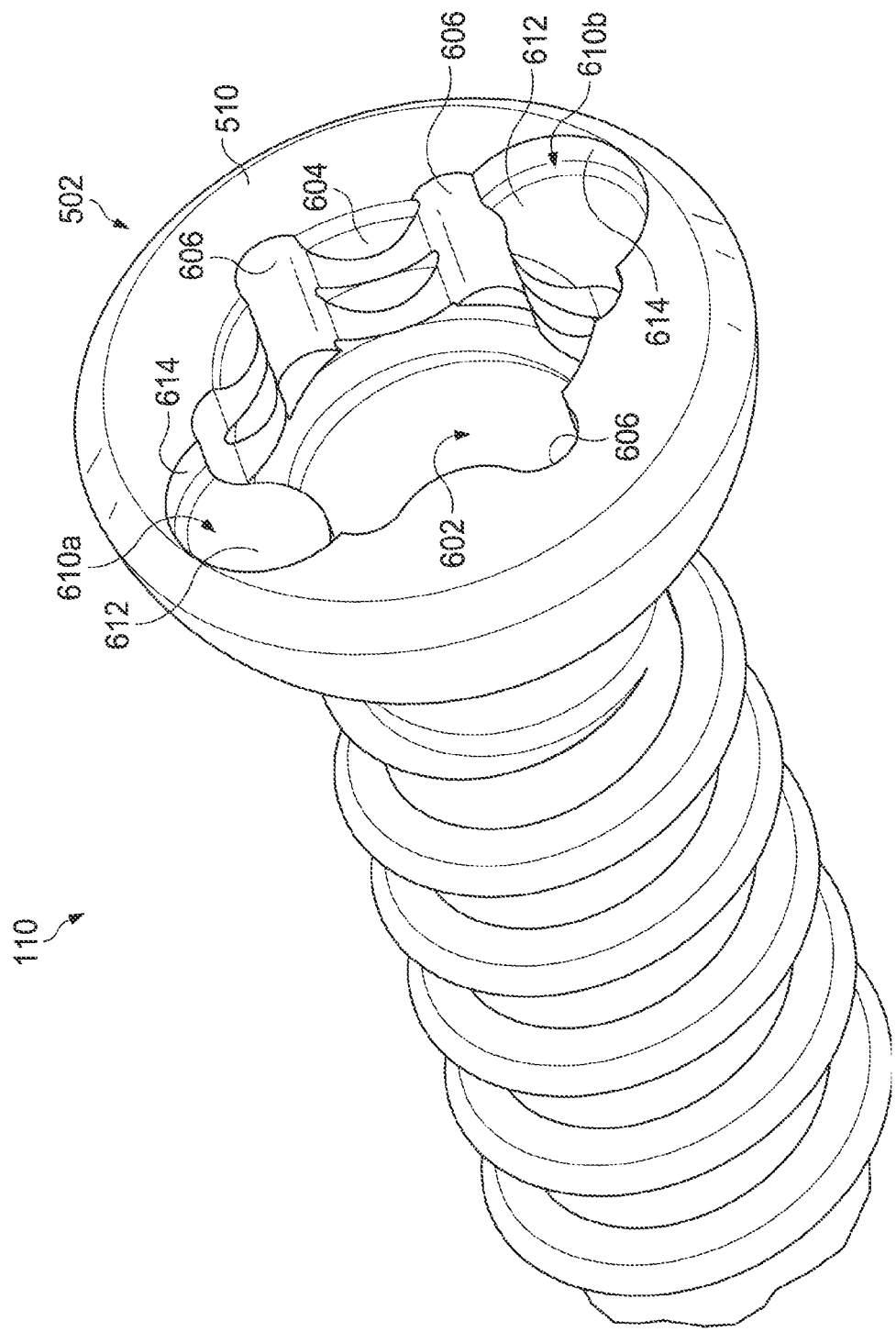
FIG. 6A is a perspective view of an exemplary fastener used with a bone fixation plate.
Figure 6B:
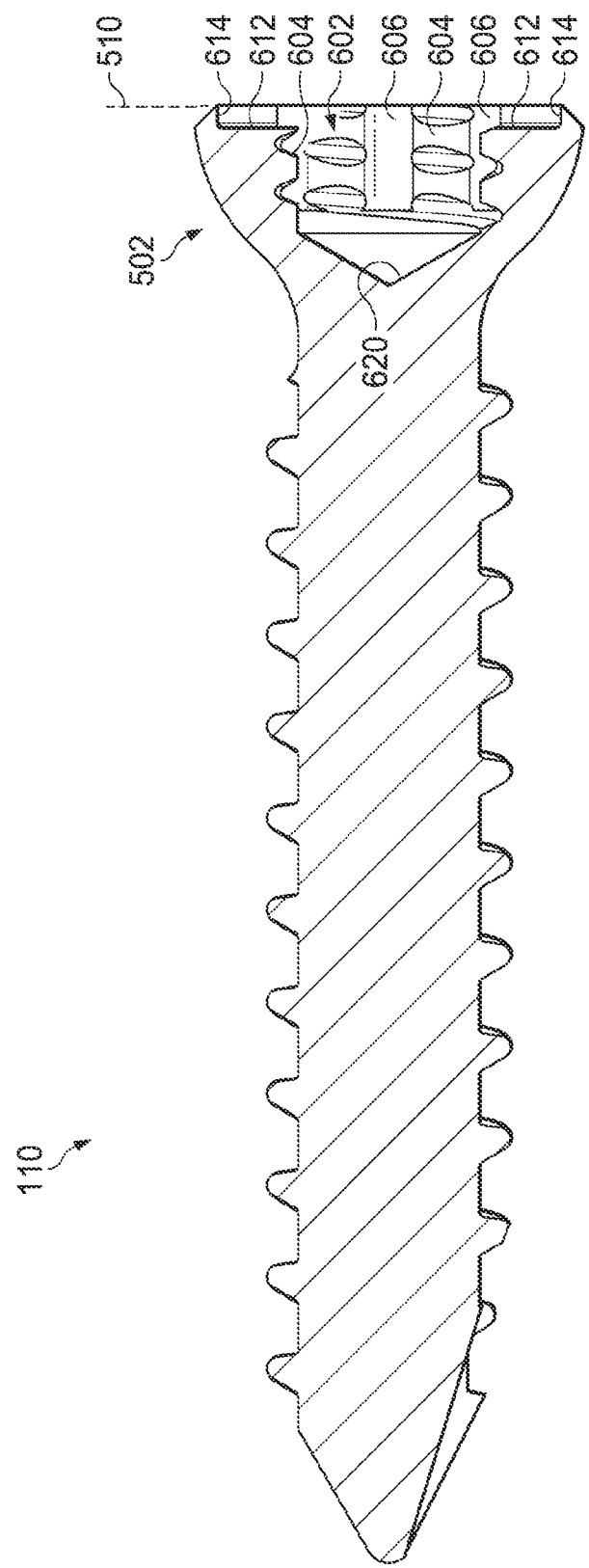
FIG. 6B is a side cutaway view of an exemplary fastener used with a bone fixation plate.

FIG. 6A is a perspective view of an exemplary fastener 110 for use with the bone fixation plate 102. FIG. 6B is a side cut away view of an exemplary fastener 110 for use with the bone fixation plate 102. As shown in FIGS. 6A and 6B, the head 502 of the fastener 110 may include a cavity 602. The cavity 602 may include multiple features configured to engage with one or more other components to assist the insertion and/or removal of the fastener 110. For example, as described in further detail below, the cavity 602 may include contoured surfaces 606, threads 604, and recesses 610a, 610b (collectively referred to as recesses 610). For the purposes of this disclosure, embodiments of cavity 602 including threads 604 may also be referred to as a threaded cavity.

As shown in FIG. 6A, the cavity 602 may include a contoured surface 606. In some embodiments, the contoured surface 606 may include multiple contours that collectively form a 6-point star-shaped pattern. The pattern of the contoured surface 606 may be engaged by a 6-point star-shaped insertion tool (for example, a screw driver with a 6-point star-shaped head) to facilitate insertion of the fastener 110 through the fastener hole 104 of the bone fixation plate 102 and into an adjacent bone during surgery. Although the contoured surface 606 is illustrated in FIG. 6B as having multiple contours that form a 6-point star-shaped pattern, the contoured surface 606 may include any number of contours to form any shape suitable for engaging an insertion tool.

As shown in FIGS. 6A and 6B, the cavity 602 may also include threads 604 and recesses 610. The threads 604 may be located between a sloped sidewall surface 620 and the first surface 510 at the top end of the head 502. As described in further detail below with respect to FIGS. 7-11, the threads 604 may correspond to threads of a removal tool. Specifically, the threads 604 may engage with threads of a removal tool to bring the removal tool into contact with the fastener 110. As the respective threads engage each other, further features of the removal tool may engage with the recesses 610. The recesses 610 may define a first surface 612 and an outer surface 614. The removal tool may apply a rotational torque to the recesses 610, and specifically to the outer surface 614 of the recesses 610, to unscrew and/or remove the fastener 110 from a bone adjacent to the bone fixation plate 102. Although FIG. 6A illustrates the recesses 610 implemented with two partial circular shapes, the fastener 110 may be implemented with any suitable number of recesses formed with any shape suitable for receiving a rotational torque for removing the fastener 110 from a body surface such as a bone, tendon, or ligament. Moreover, although the recesses 610 are illustrated in FIG. 6A as being adjacent to the cavity 602, the recesses 610 may, in some embodiments, be formed by indentations in the first surface 510 separate from and not directly adjacent to the cavity 602.

Figure 7A:
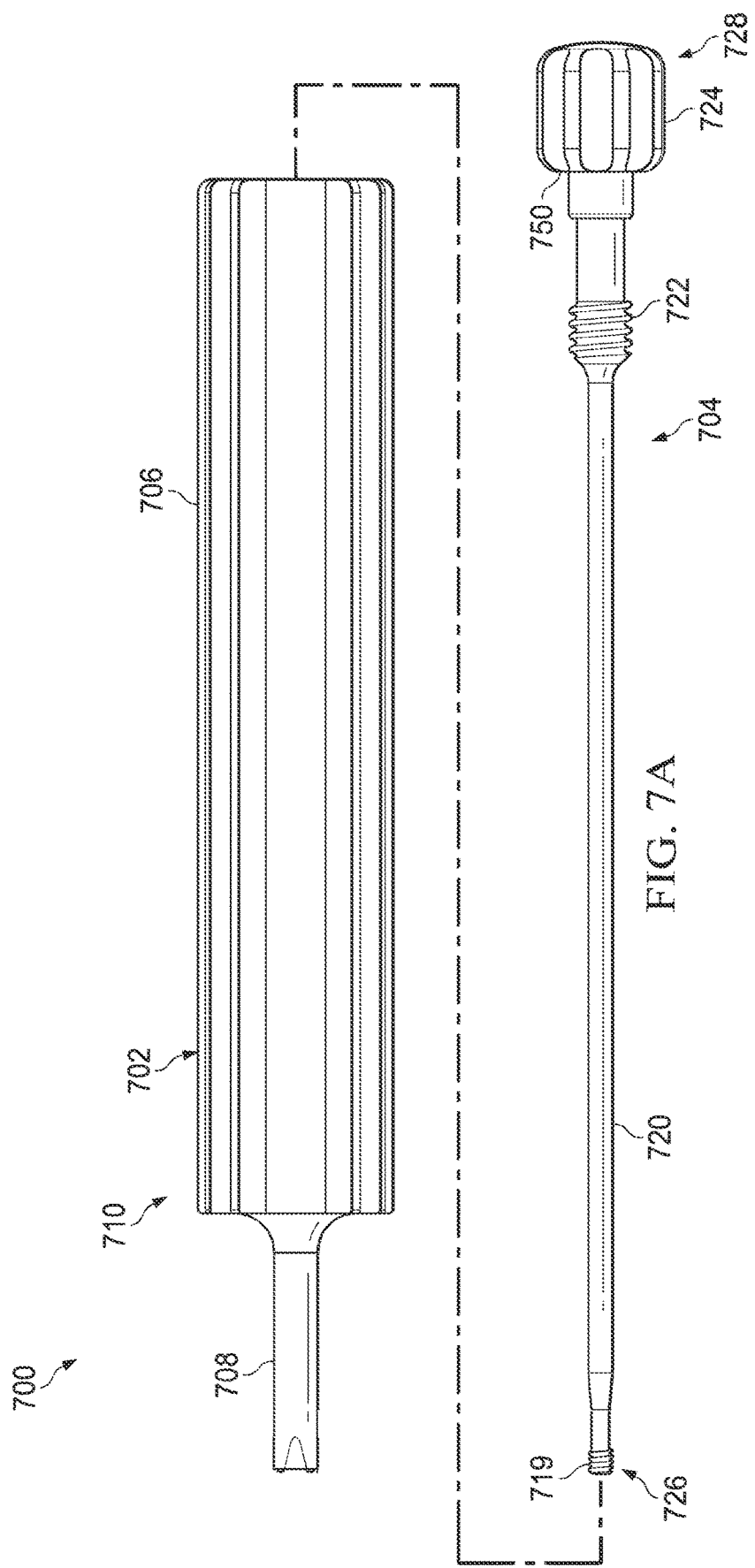
FIG. 7A is an exploded side view of an exemplary removal tool system.
Figure 7B:
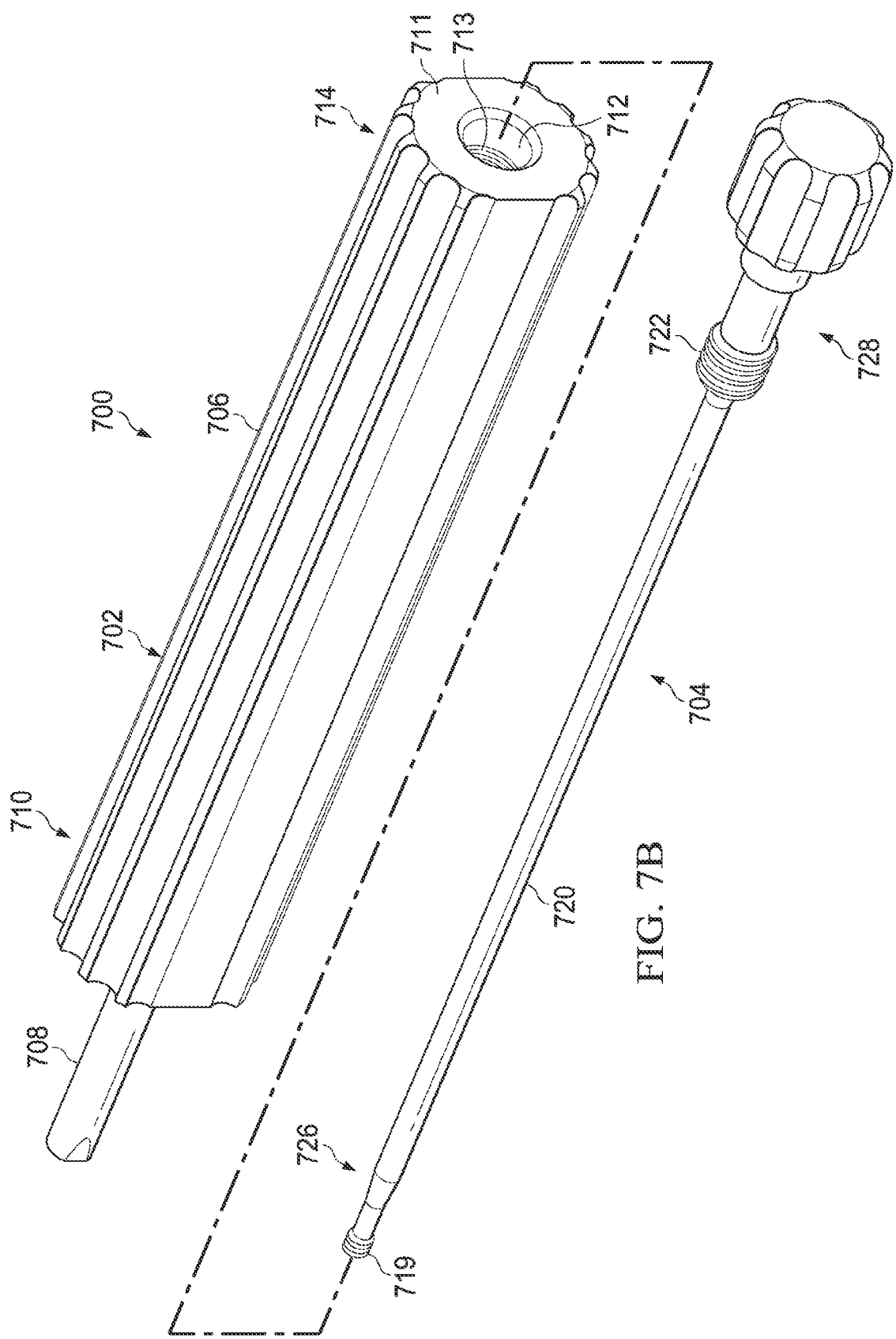
FIG. 7B is an exploded perspective view of an exemplary removal tool system.

FIG. 7A is an exploded side view of an exemplary removal tool system 700. FIG. 7B is an exploded perspective view of the exemplary removal tool system 700. The removal tool system 700 may include an outer portion 702 and an inner portion 704. The outer portion 702 may include a body 706 and a shaft 708. The shaft 708 may be coupled to the body 706 at a first end 710 of the body 706. As shown in FIG. 7B, the body 706 may include a surface 711 including a channel 712 proximate to a second end 714 of the body 706, which may be opposite to the first end 710 of the body 706. The channel 712 may include threads 713. The channel 712 of the outer portion 702 extends through the body 706 and the shaft 708. As described in further detail below, the inner portion 704 of the removal tool system 700 may extend through the channel 712 of the outer portion 702 during a removal process for the fastener 110.

The inner portion 704 of the removal tool system 700 may include first threads 719, a shaft 720, second threads 722, and a knob 724. The first threads 719 may be positioned proximate to a first end 726 of the inner portion 704. The second threads 722 and the knob 724 may be positioned proximate to a second end 728 of the inner portion 704, which may be opposite to the first end 726 of the inner portion 704. The knob 724 may include a surface 750.

As described in further detail below, first threads 719 of the inner portion 704 may pass through the channel 712 of the outer portion 702 and may engage with corresponding threads of a fastener during a removal process. Further, the second threads 722 of the inner portion 704 may engage with the threads 713 of the outer portion 702, bringing the surface 750 of the knob 724 into contact with the surface 711 of the outer portion 702. The inner portion 704 and the outer portion 702 may thus be brought into contact and connected together during steps of the removal process, as described in further detail below.

FIG. 8A is a perspective view of the exemplary removal tool system 700 with the inner portion 704 and the outer portion 702 assembled together. FIG. 8B illustrates a close-up view of a first end 710 of the shaft 708 of the outer portion 702 of the exemplary removal tool system 700. The inner portion 704 may be configured to be positioned within the outer portion 702. Specifically, the first end 726 of the inner portion 704 (shown in FIG. 7A) may be inserted into the channel 712 (shown in FIG. 7B) and through outer portion 702 such that the shaft 720 of the inner portion 704 extends through the channel 712 of the outer portion 702. As shown in FIG. 8B, the first threads 719 of the inner portion 704 may extend out of the shaft 708 of the outer portion 702 at the first end 710. The first threads 719 terminate in an end surface 802.

Additionally, as introduced above with reference to FIGS. 7A and 7B, the inner portion 704 may be inserted into the channel 712 of the outer portion 702 and rotated such that the second threads 722 of the inner portion 704 are threadably coupled to the threads 713 of the outer portion 702. The surface 750 of the knob 724 may become located proximate to the surface 711 of the body 706.

FIG. 9 is a close up view of the shaft 708 of an outer portion of the exemplary removal tool system 700. As shown in FIG. 9, the channel 712 may extend through the shaft 708. And as described above with reference to FIG. 8B, the first threads 719 of the inner portion 704 of the removal tool system 700 may extend out of the channel 712 when the inner portion 704 is coupled to/positioned within the outer portion 702 of the removal tool system 700.

The shaft 708 may include protrusions 904a, 904b (collectively referred to as protrusions 904). The example protrusions 904 shown in FIG. 9 may be configured to engage with the example recesses 610 of the fastener 110 shown in FIG. 6A. For example, the protrusions 904 may extend from an end surface 906 of the shaft 708. The protrusions 904 may be positioned proximate to the channel 712. The protrusions 904 may include a top surface 908 and a curved surface 910. The curved surface 910 is defined between the top surface 908 and the end surface 906. In some embodiments, the protrusions 904 may be positioned opposite to one another about the channel 712. In some examples, the shaft 708 includes any number of protrusions 904 suitable for engaging the recesses 610 of the fastener 110, described further herein. Although FIG. 9 illustrates the protrusions 904 implemented with two partial circular shapes, protrusions 904 may be implemented with any suitable number of protrusions formed with any shape suitable for engaging the recesses 610 of the fastener 110 (shown in FIG. 6A) and providing a rotational torque for removing the fastener 110 from a body surface such as a bone, tendon, or ligament. Moreover, although the protrusions 904a and 904b are illustrated in FIG. 9 as being positioned adjacent to the channel 712 of the shaft 708, the protrusions 904 may, in some embodiments, be positioned elsewhere on the end surface 906 not directly adjacent to the channel 712.

The shaft 708 may further include flats 920a, 920b (collectively referred to as flats 920). The flats 920 may provide a chamfered area at the end of the shaft 708. For example, the flats 920 may extend between the end surface 906 and an apex 922. The flats 920 may be angled away from the first end 710 of the body 706. As described in further detail below with respect to FIGS. 10A-10E, the flats 920 may be positioned on the shaft 708 to correspond to the position of the tabs 140 of the clip 124 in order to provide a wedging force to spread the tabs 140 of the clip 124 during a fastener removal process. The shaft 708 may include two flats 920a and 920b as shown in FIG. 9, or any other number of flats disposed around the end surface 906 suitable to engage with a number of the tabs 140 of the clip 124 during steps of a removal process for the fastener 110.

FIG. 10A is a side view of an exemplary removal tool system 700 for disengaging the fastener 110 from the bone fixation plate 102. FIG. 10B is a side view of an exemplary removal tool system 700 proximate to the bone fixation plate 102. For the purposes of this disclosure, the bone fixation plate 102, any clips and fasteners used with the bone fixation plate 102, and the removal tool system 700 may be referred to as parts of a bone fixation kit. The removal tool system 700 may engage one or more of the fasteners 110 to remove the fasteners 110 from being coupled to the bone fixation plate 102 and/or a bone 1002 (or other body part 1002). The inner portion 704 of the removal tool system 700 may be rotated in first direction (for example, clockwise) to engage the fastener 110 while the outer portion 702 of the removal tool system 700 spreads the tabs 140 of the clip 124 and also engages the fastener 110. The removal tool system 700 may then remove the fastener 110 from being coupled with the bone fixation plate 102 and/or the bone 1002 by rotating the outer portion 702 of the removal tool system 700 in a second direction (for example, counter clockwise).

As shown in FIG. 10B, the first threads 719 (which may be part of the inner portion 704 of the removal tool system 700 as shown in FIG. 7A) may extend out from the shaft 708 as the removal tool system 700 approaches the bone fixation plate 102.

Figure 10C:
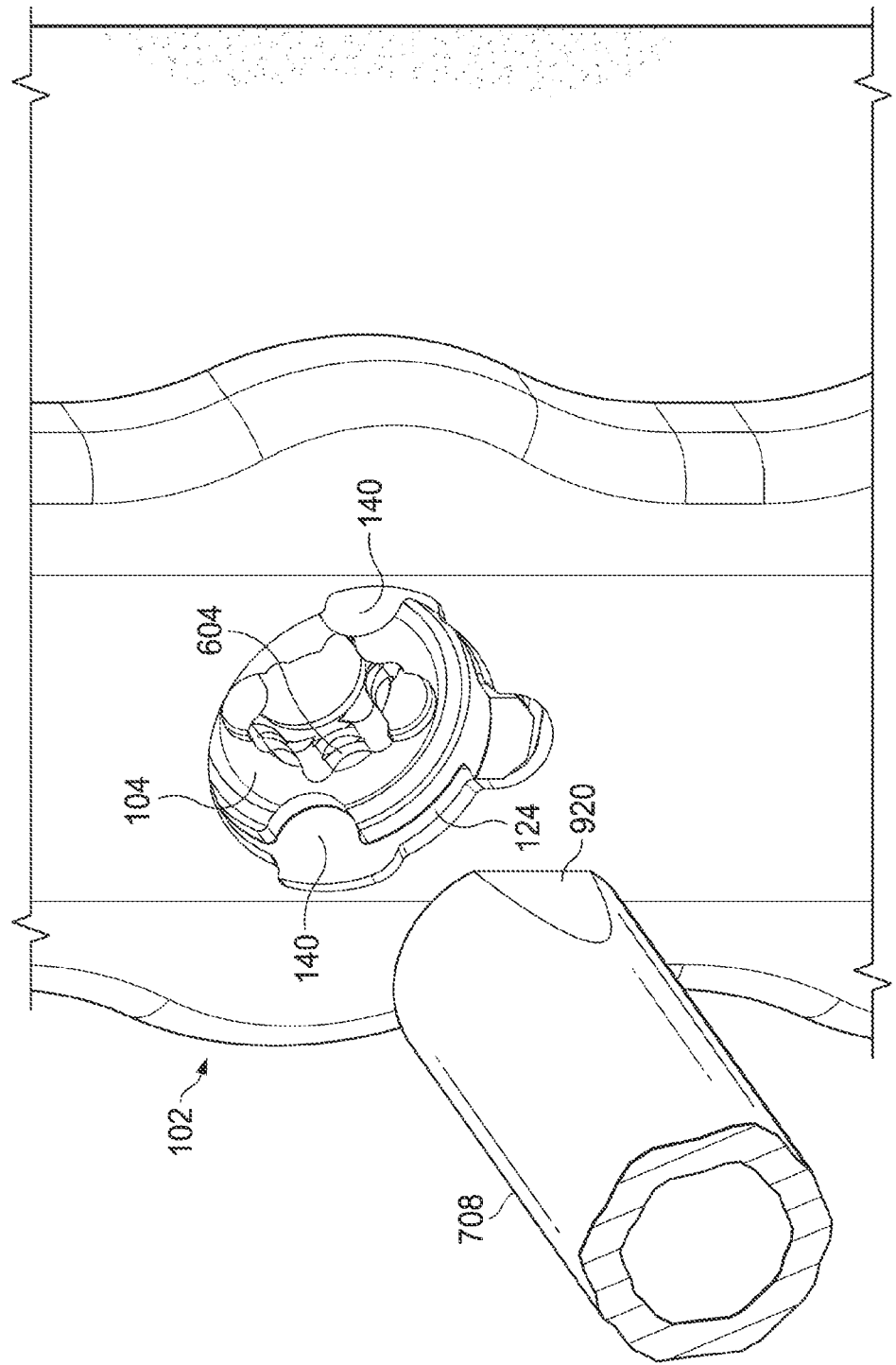
FIG. 10C is a close-up perspective view of a shaft of an exemplary removal tool system proximate to a bone fixation plate.

FIG. 10C is a close-up perspective view of the shaft 708 of the exemplary removal tool system 700 proximate to the bone fixation plate 102. As the shaft 708 of the outer portion 702 of the removal tool system 700 is brought proximate to the fastener hole 104, the flats 920 of the shaft 708 may engage the tabs 140 of the clip 124. As the shaft 708 is brought through the fastener hole 104, the flats 920 may apply a wedging force that spreads the tabs 140 outward. As described above with reference to FIGS. 2, 3A, 3B, and 3C, the clip 124 may expand outward in the cavity 118 of the fastener hole 104. For example, the clip 124 may be flexible such that as the flats 920 apply a wedging force to the tabs 140 of the clip 124, the tabs 140 of the clip 124 are moved toward and/or into the cavity 118 adjacent to the fastener hole 104. Specifically, the flats 920 exert the force on the tabs 140 to flex the clip 124 from the neutral or unflexed position over the head of the fastener 110 to a flexed position in the cavity 118 away from the head of the fastener 110.

FIG. 10D is a close-up view of the exemplary removal tool system 700 engaging with the fastener 110 used with a bone fixation plate 102. FIG. 10E is a side cutaway view of the exemplary removal tool system 700 engaging with the fastener 110 used with the bone fixation plate 102. As the shaft 708 is brought into the fastener hole 104, the first threads 719 of the inner portion 704 of the removal tool system 700 engage with the threads 604 of the fastener 110. The first threads 719 of the inner portion 704 may engage with the threads 604 of the fastener 110 until the removal tool system 700 is coupled to the fastener 110. For example, the first threads 719 of the inner portion 704 may engage the threads 604 of the fastener 110 until the end surface 802 of the first threads 719 is proximate to the sidewall surface 620 of the fastener 110. In some examples, to engage the first threads 719 of the inner portion 704 to the fastener 110, the inner portion 704 of removal tool system 700 is rotated in a first direction (for example, clockwise) until the first threads 719 of the inner portion 704 are appropriately engaged with the threads 604 of the fastener 110.

Furthermore, as the first threads 719 of the inner portion 704 engage the threads 604 of the fastener 110, the second threads 722 of the inner portion 704 (shown in FIG. 7A) may engage with the threads 713 of the outer portion 702 of the removal tool system 700. For example, referring back to FIGS. 7A, 7B, and 8A, the first threads 719 of the inner portion 704 may engage the threads 604 of the fastener 110, and the second threads 722 of the inner portion 704 may engage the threads 713 of the outer portion 702 until the surface 750 of the knob 724 of the inner portion 704 is flush against and/or abuts the surface 711 of the outer portion 702.

In response to the first threads 719 of the inner portion 704 engaging the threads 604 of the fastener 110, and the second threads 722 of the inner portion 704 engaging the threads 713 of the outer portion 702, the shaft 708 of the outer portion 702 of the removal tool system 700 may engage the fastener 110. For example, the protrusions 904 of the shaft 708 may engage with the recesses 610 of the fastener 110. In some embodiments, a curved surface 910 of the protrusions 904 (shown in FIG. 9) may engage an outer surface 614 of the recesses 610 (shown in FIG. 6A).

Figure 11:
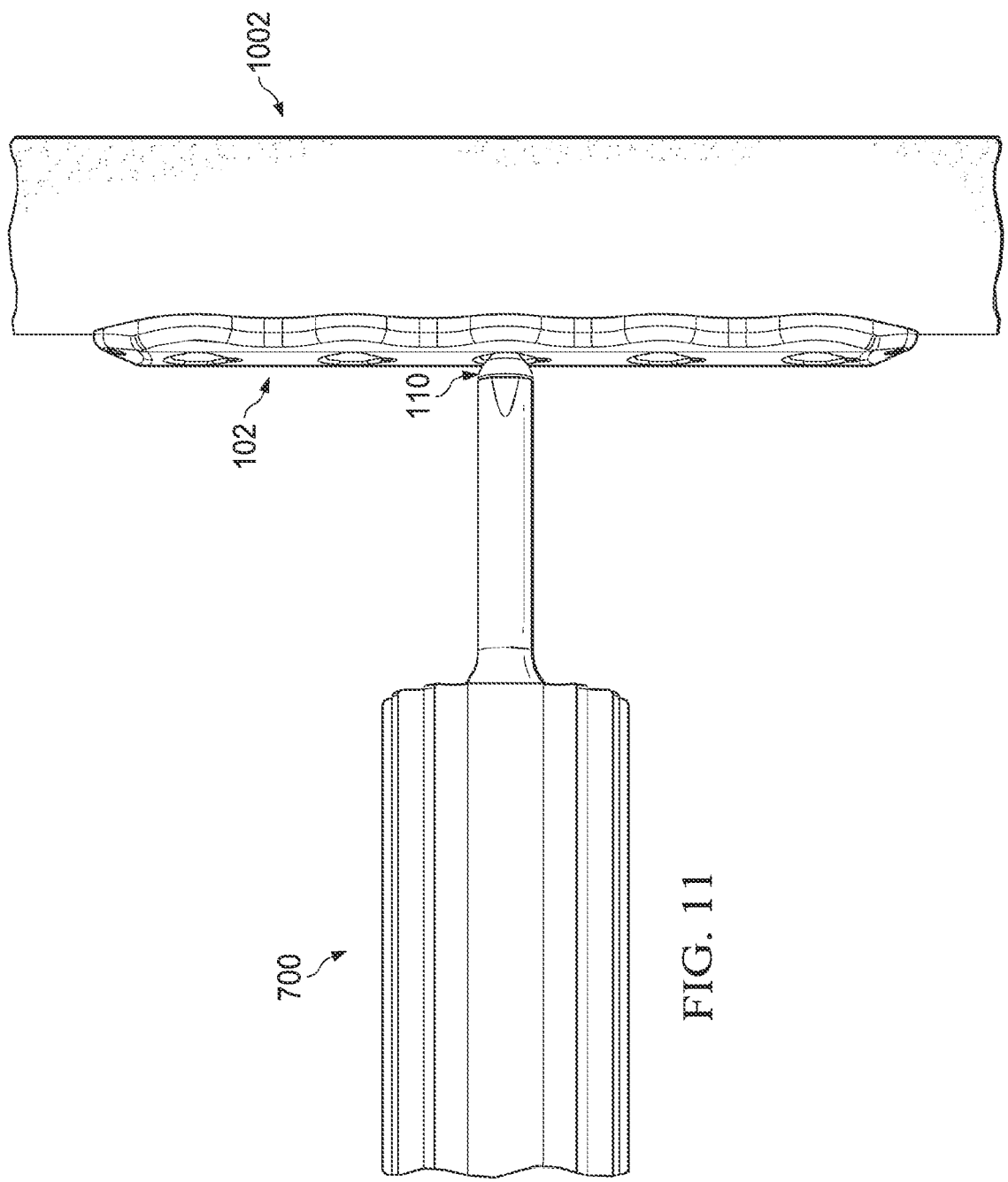
FIG. 11 is a side view of an exemplary removal tool system disengaging a fastener from a bone fixation plate.

FIG. 11 is a side view of the removal tool system 700 disengaging the fastener 110 from a bone fixation plate 102. For example, after the removal tool system 700 engages the fastener 110 as described above with reference to FIGS. 10D-10E, the removal tool system 700 may facilitate decoupling and/or removal of the fastener 110 from the bone fixation plate 102 and/or the underlying bone 1002 (or other body part 1002). Specifically, after the removal tool system 700 is coupled to the fastener 110, the outer portion 702 of the removal tool system 700 may be rotated in a second direction (for example, counter-clockwise) opposite to the first direction to disengage and decouple the fastener 110 from the bone fixation plate 102 and/or the bone 1002. In some examples, the protrusions 904 of the shaft 708 (shown in FIG. 9) may facilitate removal of the fastener 110 by providing engagement with the recesses 610 of the fastener 110 (shown in FIG. 6A), and specifically, providing leverage to the removal tool system 700 for disengage/decoupling the fastener 110 from the bone fixation plate 102 and/or the bone 1002.

In some examples, a diameter of the shaft 708 (shown in FIGS. 7A-7B) may be greater than or substantially the same as a diameter of the head 502 of the fastener 110 (shown in FIG. 4). As a result, during removal of the fastener 110 from the bone fixation plate 102, the shaft 708 may keep the tabs 140 of the clip 124 (shown in FIGS. 3A-3C) sufficiently spread to allow the head of the fastener 110 to pass back out of the fastener hole 104. For example, as the fastener 110 is brought out of the fastener hole 104 by the removal tool system 700, the shaft 708 may maintain the flexed state of the clip 124 to facilitate the removal.

Figure 12:
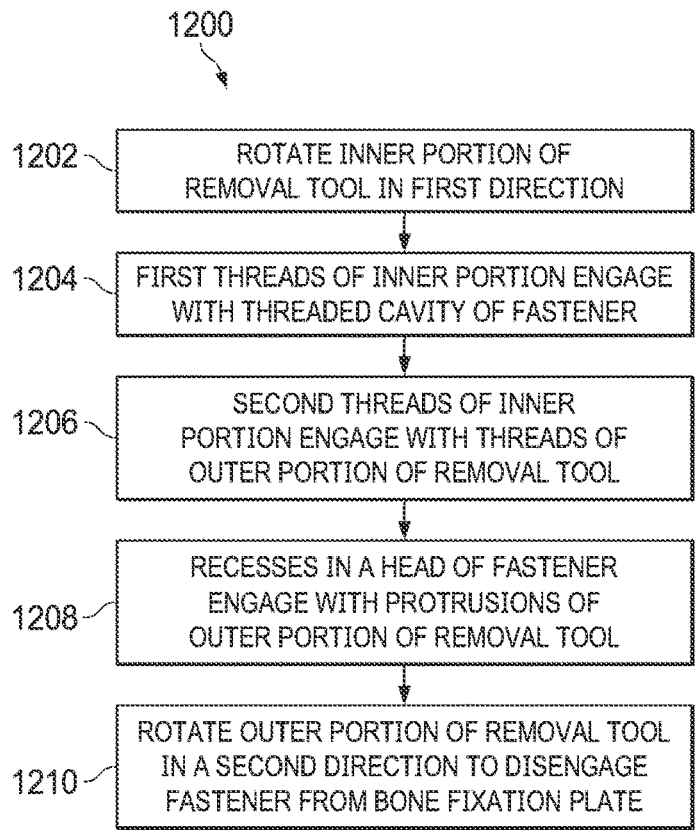
FIG. 12 illustrates a flow chart of an exemplary method for disengaging a fastener from a bone fixation plate.

FIG. 12 illustrates a flowchart of an exemplary method 1200 for disengaging a fastener from a bone fixation plate. The method 1200 may be performed by the removal tool system 700 with reference to FIGS. 1-11. It is noted that certain operations described in method 1200 may be optional or may be rearranged in different embodiments.

Method 1200 may begin and at step 1202 an inner portion of a removal tool may be rotated in a first direction. For example, the inner portion 704 of the removal tool system 700 may be rotated in a first direction (for example, clockwise), as described above with reference to FIGS. 10A and 10B.

At step 1204, the first threads of the inner portion may be engaged with a threaded cavity of a fastener in response to rotating the inner portion of the removal tool in the first direction. For example, the first threads 719 of the inner portion 704 of the removal tool system 700 may be engaged with the threads 604 of the cavity 602 of the fastener 110 in response to rotating the inner portion 704 of the removal tool system 700 in the first direction, as described above with reference to FIGS. 10D and 10E.

At step 1206, the second threads of the inner portion may be engaged with threads of an outer portion of the removal tool in response to rotating the inner portion of the removal tool in the first direction. For example, the second threads 722 of the inner portion 704 may engage the threads 713 of the outer portion 702 of the removal tool system 700 in response to rotating the inner portion 704 of the removal tool system 700 in the first direction, as described above with reference to FIGS. 7A, 7B, and 8A.

At step 1208, one or more recesses in a head of the fastener may be engaged with one or more protrusions of the outer portion of the removal tool in response to the first threads of the inner portion engaging the threaded cavity of the head of the fastener and the second threads of the inner portion engaging the threads of the outer portion of the removal tool. For example, the recesses 610 in the head 502 of the fastener 110 (shown in FIG. 6A) may be engaged by protrusions 904 of the outer portion 702 of the removal tool system 700 (shown in FIG. 9) in response to the first threads 719 of the inner portion 704 engaging with the threads 604 of the cavity 602 of the head 502 of the fastener 110 and the second threads 722 of the inner portion 704 engaging the threads 713 of the outer portion 702 of the removal tool system 700.

At step 1210, the outer portion of the removal tool may be rotated in a second direction to disengage the fastener from a bone fixation plate. The second direction may be opposite to the first direction. For example, the outer portion 702 of the removal tool system 700 may be rotated in a second direction (for example, counter clockwise) opposite to the first direction (for example, clockwise) to disengage the fastener 110 from the bone fixation plate 102, as described above with reference to FIG. 11.

Subsequently, method 1200 may end. Modifications, additions, or omissions may be made to method 1200 without departing from the scope of the disclosure. For example, the order of the steps may be performed in a different manner than that described and some steps may be performed at the same time. Additionally, each individual step may include additional steps without departing from the scope of the present disclosure.

Figure 13:
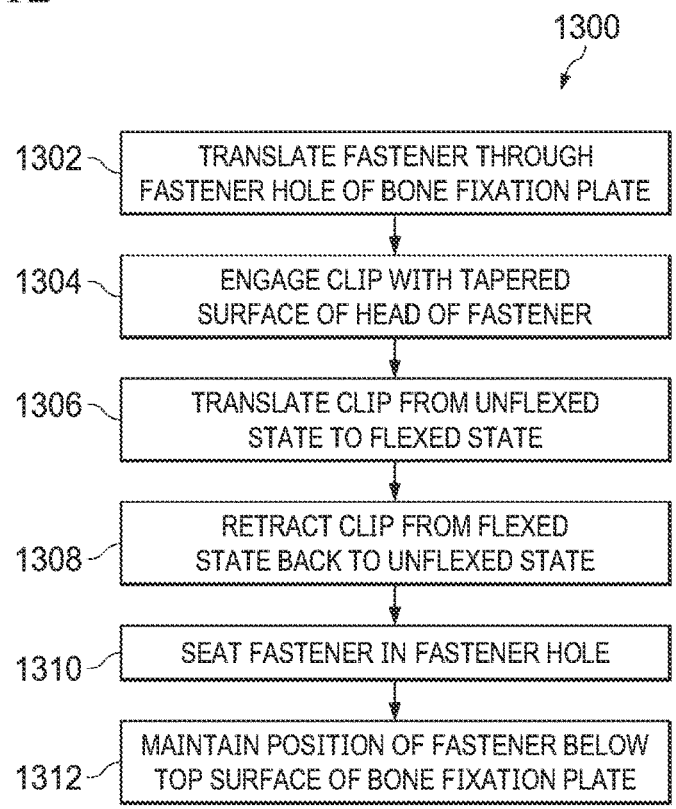
FIG. 13 illustrates a flow chart of an exemplary method for coupling a fastener and a bone fixation plate.

FIG. 13 illustrates a flow chart of an exemplary method 1300 for coupling a fastener and a bone fixation plate. The method 1300 may be performed with components described herein with reference to FIGS. 1-11. It is noted that certain operations described in method 1300 may be optional or may be rearranged in different embodiments.

Method 1300 may begin and at step 1302 a fastener may be translated through a fastener hole of a bone fixation plate into an under laying bone. For example, the fastener 110 may be translated through the fastener hole 104 of the bone fixation plate 102 (as shown in FIG. 1) and into an underlying bone (such as bone 1002 shown in FIG. 10A).

At step 1304, a clip positioned at least in part in a cavity of the bone fixation plate may be engaged with a tapered surface of the head of the fastener. For example, the clip 124 positioned at least in part in the cavity 118 of the bone fixation plate 102 (shown in FIGS. 1 and 2) may be engaged by the tapered portion 506 of the head 502 of the fastener 110 (shown in FIG. 4).

At step 1306, the clip may be translated from an unflexed state to a flexed state to allow passage of the head of the fastener past the clip. For example, the clip 124 may be translated from an unflexed state to a flexed state to allow passage of the head 502 of the fastener 110 past the clip 124, as described above with reference to FIGS. 1, 5A, and 5B.

At step 1308, the clip may retract from the flexed state back to an unflexed state after the head of the fastener has passed the clip. For example, the clip 124 may retract from the flexed state and return back to the unflexed state after the head 502 of the fastener 110 has passed the clip 124, as described above with reference to FIGS. 1, 3A-3C, and 5A-5B.

At step 1310, the fastener may be seated in the fastener hole such that the head of the fastener is positioned below a top surface of the bone fixation plate. For example, the fastener 110 may be seated in the fastener hole 104 such that the head 502 of the fastener 110 is positioned below the top surface 106 of the bone fixation plate 102, as described above with reference to FIGS. 1 and 5A-5B.

At step 1312, a position of the fastener may be maintained, with the clip, below the top surface of the bone fixation plate. For example, the position of the fastener 110 may be maintained by the clip 124 below the top surface 106 of the bone fixation plate 102, as described above with reference to FIGS. 1 and 5A-5B.

Subsequently, method 1300 may end. Modifications, additions, or omissions may be made to method 1300 without departing from the scope of the disclosure. For example, the order of the steps may be performed in a different manner than that described and some steps may be performed at the same time. Additionally, each individual step may include additional steps without departing from the scope of the present disclosure.

Embodiments herein may include:

A. A bone fixation assembly. The bone fixation assembly may include a bone fixation plate including a fastener hole and a cavity adjacent to the fastener hole. The bone fixation assembly may also include a clip. The clip may include a body having a partial circular shape, the body positioned at least partially in the cavity. The clip may also include a plurality of tabs extending inward relative to the partial circular shape of the body, each tab having a convex shape extending inward relative to the partial circular shape of the body, wherein the body and the plurality of tabs are positioned below a top surface of the bone fixation plate.

B. A bone fixation kit. The bone fixation kit may include a bone fixation plate including a fastener hole and a cavity adjacent to the fastener hole. The bone fixation kit may also include a clip. The clip may include a body having a partial circular shape, the body positioned at least partially in the cavity. The clip may also include a plurality of tabs extending inward relative to the partial circular shape of the body. In addition, the bone fixation kit may include a fastener. The fastener may include a body having screw threads and a head comprising a plurality of engagement features. The engagement features may include a threaded cavity and one or more recesses. The bone fixation kit may also include a removal tool. The removal tool may include an inner portion including first threads and second threads. The removal tool may also include an outer portion including threads and one or more protrusions. The first threads of the inner portion may be configured to engage the threaded cavity of the head of the fastener. The second threads of the inner portion may be configured to engage the threads of the outer portion. The one or more protrusions of the outer portion may be configured to engage the one or more recesses of the head of the fastener in response to the first threads of the inner portion engaging the threaded cavity of the head of the fastener and the second threads of the inner portion engaging the threads of the outer portion.

C. A method for coupling a fastener and a bone fixation plate. The method includes translating a fastener through a fastener hole of a bone fixation plate into an underlying bone. The method further includes engaging a clip positioned at least in part in a cavity of the bone fixation plate with a tapered surface of the head of the fastener. The method further includes translating the clip from an unflexed state to a flexed state to allow passage of the head of the fastener past the clip. The method further includes retracting the clip from the flexed state back to an unflexed state after the head of the fastener has passed the clip. The method further includes seating the fastener in the fastener hole such that the head of the fastener is positioned below a top surface of the bone fixation plate. The method further includes maintaining, with the clip, a position of the fastener below the top surface of the bone fixation plate.

D. A method for disengaging a fastener from a bone fixation plate. The method includes rotating an inner portion of a removal tool in a first direction. The method further includes engaging first threads of the inner portion with a threaded cavity of a fastener in response to rotating the inner portion of the removal tool in the first direction. The method further includes engaging second threads of the inner portion with threads of an outer portion of the removal tool in response to rotating the inner portion of the removal tool in the first direction. The method further includes engaging one or more recesses in a head of the fastener with one or more protrusions of the outer portion of the removal tool in response to the first threads of the inner portion engaging the threaded cavity of the head of the fastener and the second threads of the inner portion engaging the threads of the outer portion of the removal tool. The method further includes rotating the outer portion of the removal tool in a second direction to disengage the fastener from a bone fixation plate, wherein the second direction is opposite to the first direction.

Each of the embodiments A, B, C, and D may have one or more of the following additional elements in any combination. Element 1: wherein the body and the plurality of tabs of the clip have a uniform thickness. Element 2: wherein the convex shape of each tab is formed with a semi-circular shape extending inward relative to the partial circular shape of the body. Element 3: wherein the plurality of tabs includes two tabs having respective positions opposing each other around the partial circular shape of the body. Element 4: wherein the body of the clip includes two extensions, each extension extending beyond the respective position of one of the two tabs such that the partial circular shape of the body extends past 180 degrees. Element 5: wherein the bone fixation plate further includes a notch located adjacent to the fastener hole; and the clip further includes a protrusion extending from the body of the clip, the protrusion of the clip positioned within the notch of the bone fixation plate. Element 6: wherein the bone fixation plate includes a single notch for each of one or more respective fastener holes; and the single notch is located adjacent to the respective fastener hole at a position along the midline of the bone fixation plate. Element 7: wherein the clip comprises a resiliently flexible material. Element 8: wherein the cavity is radially oriented to correspond to the partial circular shape of the body of the clip; and a radius of the cavity is large than a radius of the body of the clip to allow the clip to flex outward in the clip cavity when in a displaced state. Element 9: further comprising a fastener including a body having screw threads and a head having a spherical taper. Element 10: wherein the spherical taper of the head of the fastener is configured to push outward on the plurality of tabs of the clip when the fastener is inserted into the fastener hole. Element 11: wherein the body of the clip is resiliently flexible to permit displacement of the tab to allow passage of the head of the fastener; and a spring tension of the clip in a displaced state biases the clip to return to a neutral position after the head of the fastener has passed the tab of the clip. Element 12: wherein the tab is configured to engage the head of the fastener to prevent backout of the fastener after a head of the fastener has passed the tab of the clip. Element 13: wherein the tab is configured to maintain the position of the fastener entirely below a top surface of the bone fixation plate after a head of the fastener has passed the tab of the clip. Element 14: wherein the spherical taper of the head of the fastener corresponds to a taper of the fastener hole to allow the fastener hole to receive the fastener at an angle from and including 0 degrees up to and including 45 degrees relative to a vertical axis extending through the fastener hole. Element 15: wherein the head of the fastener further comprises a chamfer adjacent to a top surface of the head of the fastener. Element 16: wherein the inner portion of the removal tool is configured to threadably engage the outer portion of the removal tool and the threaded cavity of the fastener by rotating in a first direction; and the outer portion is configured to remove the fastener by rotating in a second direction opposite from the first direction. Element 17: wherein the one or more recesses of the head of the fastener are adjacent to the threaded cavity of the head of the fastener; and the one or more protrusions of the outer portion of the removal tool are adjacent to a channel of the outer portion through which the inner portion of the removal tool passes. Element 18: wherein the one or more recesses of the head of the fastener are separated from the threaded cavity of the head of the fastener; and the one or more protrusions of the outer portion of the removal tool are separated from a channel of the outer portion through which the inner portion of the removal tool passes. Element 19: wherein the outer portion of the removal tool includes a plurality of wedging flats configured to spread respective tabs of the clip when the removal tool engages the fastener. Element 20: wherein the plurality of engagement features of the head of the fastener further includes a contoured surface configured to receive a force for inserting the fastener into bone. Element 21: wherein, maintaining, with the clip, a position of the fastener includes engaging the fastener with a convex shaped tab of the clip, the tab extending inward from a partial circular shape of a resiliently flexible body of the clip. Element 22: wherein the clip is positioned entirely below a top surface of the bone fixation plate. Element 23: further comprising preventing rotation of the clip in the cavity of the bone fixation plate with a clip protrusion positioned in a notch of the bone fixation plate. Element 24: wherein seating the fastener in the fastener hole comprises seating the fastener at an angle up to and including 45 degrees from a vertical axis extending through the fastener hole. Element 25: further comprising spreading tabs of a resiliently flexible clip located in a cavity of the bone fixation plate to allow passage of the fastener past the clip. Element 26: wherein spreading the tabs of a resiliently flexible clip includes engaging the tabs of the resiliently flexible clip with wedging flats on the outer portion of the removal tool.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, features, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

What is claimed is:

1. A bone fixation kit, comprising:
   a bone fixation plate including a fastener hole and a cavity adjacent to the fastener hole;
   a clip comprising:
   a body having a partial circular shape, the body positioned at least partially in the cavity; and
   a plurality of tabs extending inward relative to the partial circular shape of the body, wherein the body and the plurality of tabs are positioned below a top surface of the bone fixation plate; and
   a fastener comprising:
   a body having screw threads; and
   a head comprising a plurality of engagement features, the engagement features including a contoured surface configured to receive a force for inserting the fastener into bone, a threaded cavity, and one or more recesses configured to receive a force for removing the fastener; and
   a removal tool, comprising:
   an inner portion including first threads and second threads; and
   an outer portion including threads and one or more protrusions;
   wherein the first threads of the inner portion are configured to engage the threaded cavity of the head of the fastener;
   wherein the second threads of the inner portion are configured to engage the threads of the outer portion; and
   wherein the one or more protrusions of the outer portion are configured to engage the one or more recesses of the head of the fastener in response to the first threads of the inner portion engaging the threaded cavity of the head of the fastener and the second threads of the inner portion engaging the threads of the outer portion.

2. The bone fixation kit of claim 1, wherein:
   the inner portion of the removal tool is configured to threadably engage the outer portion of the removal tool and the threaded cavity of the fastener by rotating in a first direction; and
   the outer portion is configured to remove the fastener by rotating in a second direction opposite from the first direction.

3. The bone fixation kit of claim 1, wherein:
   the one or more recesses of the head of the fastener are adjacent to the threaded cavity of the head of the fastener; and the one or more protrusions of the outer portion of the removal tool are adjacent to a channel of the outer portion through which the inner portion of the removal tool passes.

4. The bone fixation kit of claim 1, wherein:

the one or more recesses of the head of the fastener are separated from the threaded cavity of the head of the fastener; and the one or more protrusions of the outer portion of the removal tool are separated from a channel of the outer portion through which the inner portion of the removal tool passes.

5. The bone fixation kit of claim 1, wherein the outer portion of the removal tool includes a plurality of wedging flats configured to spread respective tabs of the clip when the removal tool engages the fastener.

6. The bone fixation kit of claim 1, wherein the body of the clip includes two extensions, each extension extending beyond the respective position of one of the two tabs such that the partial circular shape of the body extends past 180 degrees.

7. The bone fixation kit of claim 1, wherein:

the cavity is radially oriented to correspond to the partial circular shape of the body of the clip; and a radius of the cavity is larger than a radius of the body of the clip to allow the clip to flex outward in the cavity when in a displaced state.

8. The bone fixation kit of claim 1, wherein:

the bone fixation plate includes a single notch for each of one or more respective fastener holes; and the single notch is located adjacent to the respective fastener hole at a position along a midline of the bone fixation plate.

* * * * *